(12) United States Patent
Bulla et al.

(10) Patent No.: US 7,094,554 B2
(45) Date of Patent: Aug. 22, 2006

(54) *PECTINOPHORA GOSSYPIELLA* (PINK BOLLWORM) *BACILLUS THURINGIENSIS* TOXIN RECEPTOR BT-$R_2$

(75) Inventors: Lee A. Bulla, Tioga, TX (US); Mehmet Candas, Dallas, TX (US)

(73) Assignee: The Board of Regents, The University of Texas System, Austin, TX (US)

( * ) Notice: Subject to any disclaimer, the term of this patent is extended or adjusted under 35 U.S.C. 154(b) by 563 days.

(21) Appl. No.: 10/623,366

(22) Filed: Jul. 18, 2003

(65) Prior Publication Data

US 2004/0040059 A1 Feb. 26, 2004

Related U.S. Application Data

(62) Division of application No. 09/696,115, filed on Oct. 24, 2000, now Pat. No. 6,660,497.

(60) Provisional application No. 60/161,564, filed on Oct. 26, 1999.

(51) Int. Cl.
*C07K 14/705* (2006.01)
*G01N 33/53* (2006.01)
(52) U.S. Cl. .................. 435/7.1; 530/350; 530/300; 536/23.5; 536/23.71
(58) Field of Classification Search ............ None
See application file for complete search history.

(56) References Cited

U.S. PATENT DOCUMENTS 5,693,491 A 12/1997 Bulla et al.

FOREIGN PATENT DOCUMENTS

WO    WO 98/59048    12/1998

OTHER PUBLICATIONS

Oddou et al., Immunologically unrelated Heliothis sp. and Spodoptera sp. midgut membrane-proteins bind Bacillus thringiensis cryIA(b) delta-endotoxin, Eur. J. Biochem., 212-145-150, 1993.*
Bartlett et al., Beltwide Cotton Conference (1995) 2:766.
Bulla et al., Crit. Rev. Microbiol. (1980) 8:147-204.
Hofte and Whiteley, Microbiol. Rev. (1989) 53:242.
Karim et al., Pesticide Biochemistry and Physiology (2000) 67(3):198-216.
Lee et al., Biochem. Biophys. Res. Comm. (1996) 220:575-580.
Nagamatsu et al., Biosci. Biotechnol. Biochem. (1998) 62:727-734.
Schnepf et al., Microbiol. Mol. Biol. Rev. (1998) 62:775.

* cited by examiner

*Primary Examiner*—Lorraine Spector
*Assistant Examiner*—Claire M. Kaufman
(74) *Attorney, Agent, or Firm*—Morrison & Foerster LLP

(57) ABSTRACT

A cDNA encoding a 200 kD receptor, BT-$R_2$, from the pink boll worm, *Pectinophora gossypiella*, that binds specifically to a *Bacillus thuringiensis* toxin has been cloned, sequenced and characterized. The minimum toxin binding fragment has been identified. The BT-$R_2$ cDNA permits the analysis of receptors in pink boll worm and other insects that affect crop growth and development, as well as, design assays for the cytotoxicity and binding affinity of potential pesticides. The clone and other methods described herein, permit the manipulation of natural and/or introduced homologous receptors and, thus, to specifically destroy organisms, tissues and/or cells of the target host.

6 Claims, 9 Drawing Sheets

```
AACATTTACATACAGCCAGTGTAGATGACACATTGATTTAAAAAAAATAGTGCGAGTGCTTTGA
ATCTGTGATTTCAAATATCGAATCAAAAGGACTGCATTAGTGTTGTGGGAGTTAAAGTGTTTGT
GAGAATAGACCAACGACCATGCAAGATGGCGGGTGACGCCTGCATACTGGTGACGGTGCTTCTC
ACCTTCGCAACATCAGTTTTCGGGCAAGAAACAACATCGTCGAGATGTTACTACATGACTGACG
CTATTCCGAGGGAACCGAAACCGGATGATTTGCCTGACTTAGAATGGACTGGTGGATGGACCGA
CTGGCCTTTGATCCCGGCTGAGCCAAGAGACGACGTGTGCATAAACGGCTGGTACCCACAACTC
ACCAGCACTTCTCTCGGCACCATCATCATCCACATGGAAGAGGAGATCGAGGGAGATGTTGCTA
TCGCTAAACTTAACTATGATGGTTCTGGAACCCCAGAAATTGTCCAGCCGATGGTTATAGGATC
TTCTAACCTGCTAAGTCCAGAGATCCGGAATGAAAACGGGGCGTGGTACCTTTATATAACCAAT
AGGCAAGATTATGAAACACCAACAATGCGTCGGTATACATTCGACGTCCGAGTGCCAGACGAGA
CTCGTGCGGCACGAGTGAGTCTGTCCATCGAAAACATTGACGATAACGACCCTATCGTCAGGGT
GCTAGACGCTTGCCAAGTGCCGGAATTGGGGGAGCCTCGACTAACAGACTGCGTTTACCAAGTG
TCAGACGAAGATGGGAGGCTTAGTATCGAGCCCATGACATTCCGCCTCACATCAGACCGTGAAG
ACGTACAGATATTCTATGTGGAGCCAGCTCACATTACTGGTGATTGGTTCAACATGCAAATTAC
TATCGGTATCCTATCAGCGCTTAACTTCGAAAGCAACCCGCTGCACATCTTTCAAATCACTGCT
TTGGACTCCTGGCCCAACAACCATACGGTGACGGTGATGGTGCAAGTCCAGAATGTGGAACACC
GACCGCCGCGATGGATGGAAATCTTCGCAGTCCAGCAGTTTGACGAGATGACGGAGCAGCAATT
CCAGGTGCGCGCCATCGACGGAGACACTGGCATCGGGAAAGCTATACACTATACCCTCGAGACA
GATGAGGAAGAAGATTTGTTCTTCATCGAAACACTTCCGGGCGGCCATGACGGAGCCATCTTCA
GCACTGCCATGATTGATGTGGATAGGCTCCGGCGAGATGTCTTCAGACTGTCCCTGGTGGCATA
CAAGTACGACAATGTGTCCTTCGCCACCCCGACACCCGTCGTGATCATAGTCAATGACATCAAC
AACAAGAAACCCCAACCGCTGCAAGATGAGTACACAATCTCCATAATGGAAGAAACTCCACTGT
CGCTGAATTTTGCTGAACTTTTTGGTTTCTATGATGAAGATTTGATCTACGCACAATCCTTGGT
GGAAATACAAGGCGAGAACCCTCCAGGCGTAGAGCAAGCGTTTTATATTGCGCCCACCGCAGGC
TTCCAGAACCAGACATTCGCCATAGGGACTCAAGATCACCGAATGCTGGATTATGAGGATGTTC
CTTTCCAAAACATCAAGCTCAAGGTAATAGCAACGGACCGTGACAATACCAATTTTACTGGAGT
CGCGGAAGTCAACGTGAACCTGATTAATTGGAACGACGAGGAGCCGATCTTTGAGGAAGACCAG
CTCGTTGTCAAGTTCAAGGAGACTGTACCCAAGGACTATCACGTCGGCAGACTGAGGGCTCACG
ACCGGGACATAGGAGACAGCGTTGTGCATTCCATCTTGGGAAATGCGAATACATTTTTGAGAAT
CGACGAAGAAACTGGCGACATATACGTAGCTATTGATGACGCGTTCGATTATACAGACAGAAT
GAATTTAACATACAAGTTCGCGCTCAGGACACCATGTCGGAGCCAGAGTCCAGGCATACAGCGG
CTGCTCAGCTGGTCATAGAACTCGAGGACGTCAACAACACACCTCCTACTCTGAGGCTGCCTCG
CGTAAGTCCGTCTGTAGAAGAGAATGTGCCAGAGGGCTTTGAAATCAACCGGGAGATAACCGCC
ACGGACCCTGACACCACAGCATACCTGCAGTTTGAAATAGATTGGGACACATCCTTTGCCACTA
AACAGGGGCGTGATACCAATCCAATAGAGTTCCACGGATGCGTGGATATAGAAACCATCTTCCC
AAACCCAGCCGACACCAGAGAGGCTGTGGGCGAGTGGTAGCGAAGGGGATCCGCCATAACGTG
ACCATCCATTTTGAAGAGTTTGAATTTCTCTACCTCACAGTGAGAGTTCGGGACTTGCACACAG
ATGACGGACGAGATTATGATGAATCTACCTTCACGGTAATAATAATAGATATGAACGACAACTG
GCCTATCTGGGCGTCTGGTTTCCTGAACCAGACCTTCAGTATTCGGGAGCGATCATCTACCGGC
GTCGTCATCGGGTCCGTACTCGCTACAGACATTGATGGCCCACTTTACAACCAAGTCCGGTACA
CCATTATCCCCCAGGAAGATACTCCTGAAGGTCTAGTCCAGATACATTTCGTTACGGGTCAAAT
TACAGTTGATGAGAATGGTGCAATCGACGCTGATATTCCACCTCGTTGGCACCTCAACTACACG
GTTATAGCCAGCGACAAATGTTCTGAAGAAAATGAAGAGAACTGTCCCCCGGATCCAGTGTTCT
GGGATACTCTGCGCGACAATGTAATTAACATCGTGGACATAAACAACAAGGTCCCGGCAGCAGA
CCTCAGTCGATTCAACGAAACGGTGTACATTTATGAAAATGCACCCGATTTCACGAACGTGGTC
```

Figure 1A

```
AAGATATACTCCATCGACGAAGACAGAGACGAAATATATCACACGGTGCGGTACCAGATCAATT
ATGCTGTGAACCAACGGCTGCGAGACTTCTTCGCCATAGACCTGGATTCAGGCCAGGTGTACGT
GGAGAACACCAACAATGAGCTCCTGGATCGGGACAGAGGCGAAGACCAACACAGGATATTCATT
AACCTCATTGACAACTTTTATAGCGAAGGAGATGGAAATAGAAATGTAAACACTACAGAGGTGC
TGGTGATACTATTAGATGAGAATGACAACGCTCCTGAATTGCCGACTCCAGAAGAGCTGAGTTG
GAGCATTTCCGAGGATTTACAAGAGGGTATAACACTCGATGGCGAAAGCGATGTGATATACGCA
CCGGATATAGACAAAGAGGACACGCCAAACTCTCACGTTGGCTACGCAATCCTGGCCATGACAG
TCACCAATAGAGACCTGGACACTGTTCCGAGACTTCTCAACATGCTGTCGCCTAACAACGTAAC
CGGATTCCTCCAGACAGCAATGCCTTTGAGAGGATATTGGGGGACTTACGATATAAGTGTACTG
GCGTTCGACCACGGTATTCCTCAGCAGATATCTCATGAGGTGTATGAATTGGAAATTCGACCTT
ACAATTACAATCCTCCTCAGTTCGTTTTTCCTGAATCCGGGACGATTCTACGACTGGCTTTGGA
ACGCGCAGTGGTAAATAATGTTTTGTCACTTGTAAACGGTGACCCGTTAGACAGGATACAAGCA
ATTGACGACGATGGTCTTGATGCTGGCGTGGTGACTTTCGATATTGTTGGAGATGCTGATGCGT
CAAACTACTTCAGAGTAAATAATGATGGCGACAGCTTTGGAACCTTGTTGCTGACACAGGCGCT
TCCTGAGGAAGGCAAGGAATTTGAGGTTACCATCCGGGCTACAGACGGCGGAACAGAACCTCGA
TCATATTCAACAGACTCCACTATAACAGTCCTCTTCGTTCCGACTTTGGGTGATCCGATCTTTC
AAGATAACACTTACTCAGTAGCATTCTTTGAAAAAGAGGTTGGCTTGACTGAGAGGTTCTCGCT
CCCACATGCAGAGGACCCTAAGAACAAACTCTGCACTGACGACTGTCACGATATTTACTACAGG
ATCTTTGGTGGTGTGGATTACGAGCCATTTGACCTGGACCCGGTGACGAACGTGATCTTCCTGA
AATCAGAACTAGACCGGGAGACCACTGCTACGCATGTGGTGCAAGTGGCAGCCAGTAATTCGCC
CACAGGAGGCGGAATACCACTCCCTGGGTCTCTTCTCACCGTCACTGTCACTGTACGAGAAGCG
GATCCACGGCCTGTGTTCGAGCAGCGTCTGTACACGGCTGGCATTTCCACTTCCGATAACATCA
ACAGGGAACTACTCACCGTTCGTGCAACTCATTCCGAAAACGCACAATTGACATATACCATCGA
AGACGGTTCTATGGCGGTGGACTCCACTCTGGAAGCCGTCAAGGACTCGGCGTTCCATCTGAAC
GCGCAGACCGGCGTCCTCATACTGAGGATACAACCTACTGCCAGCATGCAGGGCATGTTTGAGT
TCAACGTCATCGCTACTGACCCAGATGAGAAGACAGATACGGCAGAGGTGAAAGTCTACCTCAT
TTCATCCCAAAATAGGGTGTCCTTCATATTCCTGAACGATGTGGAGACGGTTGAGAGTAACAGA
GACTTTATCGCAGAAACGTTCAGCGTTGGCTTCAACATGACCTGCAATATAGATCAGGTGCTGC
CGGGCACCAACGACGCCGGGGTGATTCAGGAGGCCATGGCGGAAGTCCATGCTCACTTCATACA
GGATAACATCCCTGTGAGCGCCGACAGTATTGAAGAGCTTCGCAGTGACACTCAGCTGCTGCGC
TCCGTCCAAGGTGTGTTGAACCAACGGCTGTTGGTCCTGAACGACCTGGTGACGGGGGTCAGCC
CTGATCTCGGCACTGCCGGCGTGCAGATCACCATCTATGTGCTAGCCGGGTTGTCAGCCATCCT
TGCCTTCCTGTGCCTTATTCTGCTCATCACATTCATCGTGAGGACCCGAGCTCTGAACCGCCGT
TTGGAAGCACTGTCGATGACGAAATACGGCTCGGTGGATTCGGGGCTGAACCGAGTGGGGATAG
CGGCCCCAGGAACCAACAAACACGCCATCGAAGGCTCCAACCCCATCTGGAACGAGCAGATCAA
GGCCCCGGACTTCGATGCCATCAGTGACACATCTGACGACTCTGATCTAATCGGCATCGAGGAT
AGCCTGCAGGGAGACTTAGAAGAGAAAGGGCAGACAAAGCAGTAGATGCCTTGGTGAAAAAGC
TGAAGAAGAACGATGGAGCCATGGGGGAATACGAATTCAAGGCCTCTCGAGCCTCTAGAACTAT
CGTGAGTCGTATTACGTATATCCAGACATGATGAGATACATTGATGAGTTTGGACAAACCGCAA
CTAGAATGCAGTGAAAAAATGCTTTATTTGTTGAAATTTGTGATGCTATTGCTTTATTTGGAA
CCATTATAAGCTGCAATAAACAAGTTAACATCATCAATTGCATTCATTTTATGTTTCAGGTTCA
GGGGGAGGTGTGGGAGGCTATCC
```

Figure 1B

```
      SIG
   1  MAGDACILVT VLLTFATSVF GQETTSSRCY YMTDAIPREP KPDDLPDLEW
                            CR1 →
  51  TGGWTDWPLI PAEPRDDVCI NGWYPQLTST SLGTIIIHME EEIEGDVAIA
 101  KLNYDGSGTP EIVQPMVIGS SNLLSPEIRN ENGAWYLYIT NRQDYETPTM
                                                   CR2 →
 151  RRYTFDVRVP DETRAARVSL SIENIDDNDP IVRVLDACQV PELGEPRLTD
 201  CVYQVSDEDG RLSIEPMTFR LTSDREDVQI FYVEPAHITG DWFNMQITIG
                                                       CR3 →
 251  ILSALNFESN PLHIFQITAL DSWPNÑHTVT VMVQVQNVEH RPPRWMEIFA
 301  VQQFDEMTEQ QFQVRAIDGD TGIGKAIHYT LETDEEEDLF FIETLPGGHD
 351  GAIFSTAMID VDRLRRDVFR LSLVAYKYDÑ VSFATPTPVV IIVNDINNKK
              CR4 →
 401  PQPLQDEYTI SIMEETPLSL NFAELFGFYD EDLIYAQSLV EIQGENPPGV
 451  EQAFYIAPTA GFQÑQTFAIG TQDHRMLDYE DVPFQNIKLK VIATDRDNTÑ
                                        CR5 →
 501  FTGVAEVNVN LINWNDEEPI FEEDQLVVKF KETVPKDYHV GRLRAHDRDI
 551  GDSVVHSILG NANTFLRIDE ETGDIYVAID DAFDYHRQNE FNIQVRAQDT
                                CR6 →
 601  MSEPESRHTA AAQLVIELED VNNTPPTLRL PRVSPSVEEN VPEGFEINRE
 651  ITATDPDTTA YLQFEIDWDT SFATKQGRDT NPIEFHGCVD IETIFPNPAD
 701  TREAVGRVVA KGIRHÑVTIH FEEFEFLYLT VRVRDLHTDD GRDYDESTFT
                                CR7 →
 751  VIIIDMNDNW PIWASGFLÑQ TFSIRERSST GVVIGSVLAT DIDGPLYNQV
 801  RYTIIPQEDT PEGLVQIHFV TGQITVDENG AIDADIPPRW HLÑYTVIASD
                                                       CR8 →
 851  KCSEENEENC PPDPVFWDTL RDNVINIVDI NNKVPAADLS RFÑETVYIYE
 901  NAPDFTNVVK IYSIDEDRDE IYHTVRYQIN YAVNQRLRDF FAIDLDSGQV
 951  YVENTNNELL DRDRGEDQHR IFINLIDNFY SEGDGNRNVÑ TTEVLVILLD
                   CR9 →
1001  ENDNAPELPT PEELSWSISE DLQEGITLDG ESDVIYAPDI DKEDTPNSHV
1051  GYAILAMTVT NRDLDTVPRL LNMLSPNÑVT GFLQTAMPLR GYWGTYDISV
1101  LAFDHGIPQQ ISHEVYELEI RPYNYNPPQF VFPESGTILR LALERAVVNN
```

Figure 2A

```
              CR10 →
1151  VLSLVNGDPL  DRIQAIDDDG  LDAGVVTFDI  VGDADASNYF  RVNNDGDSFG

1201  TLLLTQALPE  EGKEFEVTIR  ATDGGTEPRS  YSTDSTITVL  FVPTLGDPIF
                              CR11→                   MBF
1251  QDNTYSVAFF  EKEVGLTERF  SLPHAEDPKN  KLCTDDCHDI  YYRIFGGVDY

1301  EPFDLDPVTN  VIFLKSELDR  ETTATHVVQV  AASNSPTGGG  IPLPGSLLTV
                  CR12→
1351  TVTVREADPR  PVFEQRLYTA  GISTSDNINR  ELLTVRATHS  ENAQLTYTIE

1401  DGSMAVDSTL  EAVKDSAFHL  NAQTGVLILR  IQPTASMQGM  FEFNVIATDP
                              ⌐→  MPD
1451  DEKTDTAEVK  VYLISSQNRV  SFIFLNDVET  VESNRDFIAE  TFSVGFÑMTC
                                                                  LZ
1501  NIDQVLPGTN  DAGVIQEAMA  EVHAHFIQDN  IPVSADSIEE  LRSDTQLLRS

1551  VQGVLNQRLL  VLNDLVTGVS  PDLGTAGVQI  TIYVLAGLSA  ILAFLCLILL
        →    CYT
1601  ITFIVRTRAL  NRRLEALSMT  KYGSVDSGLN  RVGIAAPGTN  KHAIEGSNPI

1651  WNEQIKAPDF  DAISDTSDDS  DLIGIEDSLQ  GDLEEKRADK  AVDALVKKLK

1701  KNDGAMGEYE  FKASRASRTI  VSRITYIQT.
```

```
1    M G V D V R I L A T L L I Y - A E T V L A Q E - - - - R C G F M V - A I P R P   B.mori BTR175
1    M A V D V R I - A A F L L V F I A P A V L A Q E - - - - R C G Y M T - A I P R L   THW BTR1
1    M A G D A C I L V T V L L T F - A T S V F G Q E T T S S R C Y Y M T D A I P R E   PBW BTR2

35   P R P D - L P E L D F E G Q T W S Q R P L I P A A D R E D V C M D G - Y H A M T   B.mori BTR175
35   P R P D N L P V L N F E G Q T W S Q R P L L P A P E R D D L C M D A - Y H V I T   THW BTR1
40   P K P D D L P D L E W T G - G W T D W P L I P A E P R D D V C I N G W Y P Q L T   PBW BTR2

73   P T - Y G T Q I I Y M E E I E G E V P I A K L N Y R G P N V P Y I E P A F L S     B.mori BTR175
74   A N - L G T Q V I Y M D E E I E D E I T I A I L N Y N G P S T P F I E L P F L S   THW BTR1
79   S T S L G T I I I H M E E E I E G D V A I A K L N Y D G S G T P E I V Q P M V I   PBW BTR2

112  G S F N L L V P V I R R I P D S N G E W H L I I T Q R Q D Y E T P G M Q Q Y V F   B.mori BTR175
113  G S Y N L L M P V I R R V - - D N G E W H L I I T Q R Q H Y E L P G M Q Q Y M F   THW BTR1
119  G S S N L L S P E I R - - - N E N G A W Y L Y I T N R Q D Y E T P T M R R Y T F   PBW BTR2

152  N I R I D G E T L V A G V S L L I V N I D D N A P I I Q A L E P C Q V D E L G E   B.mori BTR175
151  N V R V D G Q S L V A G V S L A I V N I D D N A P I I Q N F E P C R V P E L G E   THW BTR1
156  D V R V P D E T R A A R V S L S I E N I D D N D P I V R V L D A C Q V P E L G E   PBW BTR2

192  A R L T E C V Y V V T D A D G R I S T Q F M Q F R I D S D R G D D K I F Y I Q G   B.mori BTR175
191  P G L T E C T Y Q V S D A D G R I S T E F M T F R I D S V R G D E E T F Y I E R   THW BTR1
196  P R L T D C V Y Q V S D E D G R L S I E P M T F R L T S D R E D V Q I F Y V E P   PBW BTR2

232  A N I P G E W I R M T M T V G I N E P L N F E T N P L H I F S V T A L D S L P N   B.mori BTR175
231  T N I P N Q W M W L N M T I G V N T S L N F V T S P L H I F S V T A L D S L P N   THW BTR1
236  A H I T G D W F N M Q I T I G I L S A L N F E S N P L H I F Q I T A L D S W P N   PBW BTR2

272  T H T V T L M V Q V E N V E H R P P R W V E I F A V Q Q F D E K T A Q S F P V R   B.mori BTR175
271  T H T V T M M V Q V A N V N S R P P R W L E I F A V Q Q F E E K S Y Q N F T V R   THW BTR1
276  N H T V T V M V Q V Q N V E H R P P R W M E I F A V Q Q F D E M T E Q F Q V R     PBW BTR2

312  A I D G D T G I N K P I H Y R L E T A E E D T F F H I R T I E G G R S G A I L Y   B.mori BTR175
311  A I D G D T E I N M P I N Y R L I T N E E D T F F S I E A L P G G K S G A V F L   THW BTR1
316  A I D G D T G I G K A I H Y T L E T D E E D L F I E T L P G G H D G A I F S       PBW BTR2

352  V D P I D R D T L Q R E V F Q L S I I A Y K Y D N E S S A T A A N V V I I V N D   B.mori BTR175
351  V S P I D R D T L Q R E V F P L T I V A Y K Y D E E A F S T S T N V V I I V T D   THW BTR1
356  T A M I D V D R L R R D V F R L S L V A Y K Y D N V S F A T P T P V V I I V N D   PBW BTR2

392  I N D Q R P E P L F K E Y R L N I M E E T A L T L N F D Q E F G F H D R D L G Q   B.mori BTR175
391  I N D Q R P E P I H K E Y R L A I M E E T P L T L N F D K E F G F H D K D L G Q   THW BTR1
396  I N N K K P Q P L Q D E Y T I S I M E E T P L S L N F A E L F G F Y D E D L - I   PBW BTR2

432  N A Q Y T V R L E S D Y P A D A A K A F Y I A P E V G Y Q R Q T F I M G T A N H   B.mori BTR175
431  N A Q Y T V R L E S V D P P G A A E A F Y I A P E V G Y Q R Q T F I M G T L N H   THW BTR1
435  Y A Q S L V E I Q G E N P P G V E Q A F Y I A P T A G F Q N Q T F A I G T Q D H   PBW BTR2

472  K M L D Y E - V P E F Q R I R L R V I A T D M D N E E H V G V A Y V Y I N L I N   B.mori BTR175
471  S M L D Y E - V P E F Q S I T I R V A T D N N D T R H V G V A L V H I D L I N     THW BTR1
475  R M L D Y E D V P - F Q N I K L K V I A T D R D N T N F T G V A E V N V N L I N   PBW BTR2

511  W N D E P I F E H S V Q N V S F K E T E G K G F F V A N V R A H D R D I D D R     B.mori BTR175
510  W N D E Q P I F E H A V Q T V T F D E T E G E G F F V A K A V A H D R D I G D V   THW BTR1
514  W N D E P I F E E D Q L V V K F K E T V P K D Y H V G R L R A H D R D I G D S     PBW BTR2

551  V E H T L M G N A N N Y L S I D K D T G D I H V T Q D D F F D Y H R Q S E L F V   B.mori BTR175
550  V E H T L L G N A V N F L T I D K L T G D I R V S A N D S F N Y H R E S E L F V   THW BTR1
554  V V H S I L G N A N T F L R I D E E T G D I Y V A I D D A F D Y H R Q N E F N I   PBW BTR2
```

Figure 5B

```
591  QVRADDTLGEP--FHTATSQLLIHLEDINNTPPTLRLPRG    B.mori BTR175
590  QVRATDTLGEP--FHTATSQLVIRLNDINNTPPTLRLPRG    THW BTR1
594  QVRAQDTMSEPESRHTAAAQLVIELEDVNNTPPTLRLPRV    PBW BTR2

629  SPNVEENVPEGYIITSEIRATPDTTAELRFEIDWTTSYA     B.mori BTR175
628  SPQVEENVPDGHVITQELRATDPDTTADLRFEINWDTSFA    THW BTR1
634  SPSVEENVPEGFEINREITATDPDTTAYLQFEIDWDTSFA    PBW BTR2

669  TKQGREANPIEFHNCVEIETIYPAINNRGSAIGRLVVKKI    B.mori BTR175
668  TKQGRQANPDEFRNCVEIETIFPEINNRGLAIGRVVAREI    THW BTR1
674  TKQGRDTNPIEFHGCVDIETIFPNPADTREAVGRVVAKGI    PBW BTR2

709  RENVTIDYEEFEMLYLTVRVRDLNTVIGDDYDESTFTITI    B.mori BTR175
708  RHNVTIDYEEFEVLSLTVRVRDLNTVYGDDYDESMLTITI    THW BTR1
714  RHNVTIHFEEFEFLYLTVRVRDLHTDDGRDYDESTFTVII    PBW BTR2

749  IDMNDNPPIWVPGTLEQSLRVREMSDAGVVIGLTATDID    B.mori BTR175
748  IDMNDNAPVWVEGTLEQNFRVREMSAGGLVVGSVRADDID    THW BTR1
754  IDMNDNWPIWASGFLNQTFSIRERSSTGVVIGSVLATDID    PBW BTR2

789  GPLYNQVRYTMKANEGTPENLLMIDFYTGQITVKTSGAID    B.mori BTR175
788  GPLYNQVRYTIFPREDTDKDLIMIDFLTGQISVNTSGAID    THW BTR1
794  GPLYNQVRYTIIPQEDTPEGLVQIHFVTGQITVDENGAID    PBW BTR2

829  ADVPRRYNLYYTVVATDRCYAEDPDDCPDPTYWETPGQV    B.mori BTR175
828  ADTPPRFHLYYTVVASDRCSTEDPADCPPDPTYWETEGNI    THW BTR1
834  ADIPPRWHLNYTVIASDKCSEENEENCPPDPVFWDTLRDN    PBW BTR2

869  VIQIDTNNKIPQPETDQFKAVVYIYEDAVSGDEVVKVIG    B.mori BTR175
868  TIHITDTNNKVPQAETTKFDTVVYIYENATHLDEVVTLIA    THW BTR1
874  VINIVDINNKVPAADLSRFNETVYIYENAPDFTNVVKIYS   PBW BTR2

909  SDLDRDDIYHTIRYQINYAVNPRLRDFFAVDPDTGRVYVY    B.mori BTR175
908  SDLDRDEIYHTVSYVINYAVNPRLMNFFSVNRETGLVYVD   THW BTR1
914  IDEDRDEIYHTVRYQINYAVNQRLRDFFAIDLDSGQVVV-   PBW BTR2

949  YTTD---EVLDRDGDEPQHRIFFNLIDNFQQGDGNRNQN    B.mori BTR175
948  YETQGSGEVLDRDGDEPTHRIFFNLIDNFMGEGNRNQN     THW BTR1
953  --ENTNNELLDRDRGEDQHRIFINLIDNFYSEGDGNRNVN   PBW BTR2

986  DAEVLVVLLDVNDNAPELPEPDELSWSVSESLTKGTRLQP    B.mori BTR175
988  DTEVLVILLDVNDNAPELPPPSELSWTISENLKQGVRLEP    THW BTR1
991  TTEVLVILLDENDNAPELPTPEELSWSISEDLQEGITLDG    PBW BTR2

1026 H---IYAPDRDEPDTDNSRVGYAIISLTIANREIE-VPEL    B.mori BTR175
1028 H---IFAPDRDEPDTDNSRVGYEILNLS-TERDIE-VPEL    THW BTR1
1031 ESDVIYAPDIDKEDTPNSHVGYAILAMTVTNRDLDTVPRL    PBW BTR2

1062 FTMIQIQNVTGELETAMDLRGYWGTYAIHIKAYDHGIPQQ    B.mori BTR175
1063 FVMIQIANVTGELETAMDLKGYWGTYAIHIRAFDHGIPQ-    THW BTR1
1071 LNMLSPNNVTGFLQTAMPLRGYWGTYDISVLAFDHGIPQQ    PBW BTR2

1102 MS-NETYELVIRPYNFHAPVFVFPKHGATLRLARERAVVN    B.mori BTR175
1102 MSMNETYELIIHPFNYYAPEFVFPTNDAVIRLARERAVIN    THW BTR1
1111 IS-HEVYELIRPYNYNPPQFVFPESGTILRLALERAVVN    PBW BTR2

1141 GLLATVDGEFLNRIVATDEDGLHAGQVAFEVVGDTEAVDY    B.mori BTR175
1142 GVLATVNGEFLERISATDPDGLHAGVVTFQVVGDEESQRY    THW BTR1
1150 NVLSLVNGDPLDRIQAIDDDGLDAGVVTFDIVGDADASNY    PBW BTR2
```

Figure 5C

SEQUENCE LISTING

<160> NUMBER OF SEQ ID NOS: 18

<210> SEQ ID NO 1
<211> LENGTH: 5527
<212> TYPE: DNA
<213> ORGANISM: Pectinophora gossypiella

<400> SEQUENCE: 1

```
aacatttaca tacagccagt gtagatgaca cattgattta aaaaaaatag tgcgagtgat      60
ttgaatctgt gatttcaaat atagaatcaa aaggactgca ttagtgttgt gggagttaaa     120
gtgtttgtga aatagacca acgaccatgc aagatggcgg gtgacgcctg catactggtg     180 acgtgcttc tcaccttcgc aacatcagtt ttcgggcaag aaacaacatc gtcgagatgt      240
tactacatga ctgacgctat tccgagggaa ccgaaccgg atgatttgcc tgacttagaa      300
tggactggtg gatggaccga ctggcctttg atcccggctg agccaagaga cgacgtgtgc     360
ataaacggct ggtacccaca actcaccagc acttctctcg gcaccatcat catccacatg     420
gaagaggaga tcgagggaga tgttgctatc gctaaactta actatgatgg ttctggaacc     480
ccagaaattg tccagccgat ggttatagga tcttctaacc tgctaagtcc agagatccgg     540
aatgaaaacg gggcgtggta cctttatata accataggc aagattatga aacaccaaca      600
atgcgtcggt atacattcga cgtccgagtg ccagacgaga ctcgtgcggc acgagtgagt     660
ctgtccatcg aaaacattga cgataacgac cctatcgtca gggtgctaga cgcttgccaa     720
gtgccggaat tggggagcc tcgactaaca gactgcgttt accaagtgtc agacgaagat     780
gggaggctta gtatcgagcc catgacattc cgcctcacat cagaccgtga agacgtacag     840
atattctatg tggagccagc tcacattact ggtgattggt tcaacatgca aattactatc     900
ggtatcctat cagcgcttaa cttcgaaagc aacccgctgc acatctttca aatcactgct     960
ttggactcct ggcccaacaa ccatacggtg acggtgatgt gcaagtcca gaatgtggaa    1020 caccgaccgc cgcgatggat ggaaatcttc gcagtccagc agtttgacga gatgacggag    1080
cagcaattcc aggtgcgcgc catcgacgga gacactggca tcgggaaagc tatacactat    1140
accctcgaga cagatgagga agaagatttg ttcttcatcg aaacacttcc gggcggccat    1200
gacggagcca tcttcagcac tgccatgatt gatgtggata ggctccggcg agatgtcttc    1260
agactgtccc tggtggcata caagtacgac aatgtgtcct tcgccacccc gacacccgtc    1320
gtgatcatag tcaatgacat caacaacaag aaacccaac cgctgcaaga tgagtacaca    1380
atctccataa tggaagaaac tccactgtcg ctgaattttg ctgaactttt tggtttctat    1440
gatgaagatt tgatctacgc acaatccttg gtggaaatac aaggcgagaa ccctccaggc    1500
gtagagcaag cgttttatat tgcgcccacc gcaggcttcc agaaccagac attcgccata    1560
gggactcaag atcaccgaat gctggattat gaggatgttc ctttccaaaa catcaagctc    1620
aaggtaatag caacggaccg tgacaatacc aattttactg gagtcgcgga agtcaacgtg    1680
aacctgatta attggaacga cgaggagccg atctttgagg aagaccagct cgttgtcaag    1740
ttcaaggaga ctgtacccaa ggactatcac gtcggcagac tgagggctca cgaccgggac    1800
ataggagaca gcgttgtgca ttccatcttg ggaaatgcga atacattttt gagaatcgac    1860
```

-continued

```
gaagaaactg gcgacatata cgtagctatt gatgacgcgt tcgattatca cagacagaat    1920
gaatttaaca tacaagttcg cgctcaggac accatgtcgg agccagagtc caggcataca    1980
gcggctgctc agctggtcat agaactcgag gacgtcaaca acacacctcc tactctgagg    2040
ctgcctcgcg taagtccgtc tgtagaagag aatgtgccag agggctttga aatcaaccgg    2100
gagataaccg ccacggaccc tgacaccaca gcatacctgc agtttgaaat agattgggac    2160
acatcctttg ccactaaaca ggggcgtgat accaatccaa tagagttcca cggatgcgtg    2220
gatatagaaa ccatcttccc aaacccagcc gacaccagag aggctgtggg gcgagtggta    2280
gcgaagggga tccgccataa cgtgaccatc cattttgaag agtttgaatt tctctacctc    2340
acagtgagag ttcgggactt gcacacagat gacggacgag attatgatga atctaccttc    2400
acggtaataa taatagatat gaacgacaac tggcctatct gggcgtctgg tttcctgaac    2460
cagaccttca gtattcggga gcgatcatct accggcgtcg tcatcgggtc cgtactcgct    2520
acagacattg atgcccact ttacaaccaa gtccggtaca ccattatccc ccaggaagat    2580
actcctgaag gtctagtcca gatacatttc gttacgggtc aaattacagt tgatgagaat    2640
ggtgcaatcg acgctgatat tccacctcgt tggcacctca actacacggt tatagccagc    2700
gacaaatgtt ctgaagaaaa tgaagagaac tgtcccccgg atccagtgtt ctgggatact    2760
ctgcgcgaca atgtaattaa catcgtggac ataaacaaca aggtcccggc agcagacctc    2820
agtcgattca acgaaacggt gtacatttat gaaaatgcac ccgatttcac gaacgtggtc    2880
aagatatact ccatcgacga agacagagac gaaatatatc acacggtgcg gtaccagatc    2940
aattatgctg tgaaccaacg gctgcgagac ttcttcgcca tagacctgga ttcaggccag    3000
gtgtacgtgg agaagaccaa caatgagctc ctggatcggg acagaggcga agaccaacac    3060
aggatattca ttaacctcat tgacaacttt tatagcgaag gagatggaaa tagaaatgta    3120
aacactacag aggtgctggt gatactatta gatgagaatg caacgctcc tgaattgccg    3180 actccagaag agctgagttg gagcatttcc gaggatttac aagagggtat aacactcgat    3240
ggcgaaagcg atgtgatata cgcaccggat atagacaaag aggacacgcc aaactctcac    3300
gttggctacg caatcctggc catgacagtc accaatagac acctggacac tgttccgaga    3360
cttctcaaca tgctgtcgcc taacaacgta accggattcc tccagacagc aatgcctttg    3420
agaggatatt gggggactta cgatataagt gtactggcgt tcgaccacgg tattcctcag    3480
cagatatctc atgaggtgta tgaattggaa attcgacctt acaattacaa tcctcctcag    3540 ttcgttttc ctgaatccgg gacgattcta cgactggctt tggaacgcgc agtggtaaat    3600
aatgttttgt cacttgtaaa cggtgacccg ttagacagga tacaagcaat tgacgacgat    3660
ggtcttgatg ctggcgtggt gactttcgat attgttggag atgctgatgc gtcaaactac    3720
ttcagagtaa ataatgatgg cgacagcttt ggaaccttgt tgctgacaca ggcgcttcct    3780
gaggaaggca aggaatttga ggttaccatc cgggctacag acggcggaac agaacctcga    3840
tcatattcaa cagactccac tataacagtc ctcttcgttc cgactttggg tgatccgatc    3900
tttcaagata acacttactc agtagcattg tttgaaaaag aggttggctt gactgagagg    3960
ttctcgctcc cacatgcaga ggaccctaag aacaaactct gcactgacga ctgtcacgat    4020
atttactaca ggatctttgg tggtgtggat tacgagccat ttgacctgga cccggtgacg    4080
aacgtgatct tcctgaaatc agaactagac cgggagacca ctgctacgca tgtggtgcaa    4140
gtggcagcca gtaattcgcc cacaggaggc ggaataccac tccctgggtc tcttctcacc    4200
gtcactgtca ctgtacgaga agcggatcca cggcctgtgt tcgagcagcg tctgtacacg    4260
```

-continued

```
gctggcattt ccacttccga taacatcaac agggaactac tcaccgttcg tgcaactcat    4320
tccgaaaacg cacaattgac atataccatc gaagacggtt gtatggcggt ggactccact    4380
ctggaagccg tcaaggactc ggcgttccat ctgaacgcgc agaccggcgt cctcatactg    4440
aggatacaac ctactgccag catgcagggc atgtttgagt tcaacgtcat cgctactgac    4500
ccagatgaga agacagatac ggcagaggtg aaagtctacc tcatttcatc ccaaaatagg    4560
gtgtccttca tattcctgaa cgatgtggag acggttgaga gtaacagaga ctttatcgca    4620
gaaacgttca gcgttggctt caacatgacc tgcaatatag atcaggtgct gccgggcacc    4680
aacgacgccg gggtgattca ggaggccatg gcggaagtcc atgctcactt catacaggat    4740
aacatccctg tgagcgccga cagtattgaa gagcttcgca gtgacactca gctgctgcgc    4800
tccgtccaag gtgtgttgaa ccaacggctg ttggtcctga cgacctggt gacggggtc    4860 agccctgatc tcggcactgc cggcgtgcag atcaccatct atgtgctagc cgggttgtca    4920
gccatccttg ccttcctgtg ccttattctg ctcatcacat tcatcgtgag gacccgagct    4980
ctgaaccgcc gtttggaagc actgtcgatg acgaaatacg gctcggtgga ttcggggctg    5040
aaccgagtgg ggatagcggc cccaggaacc aacaaacacg ccatcgaagg ctccaacccc    5100
atctggaacg agcagatcaa ggccccggac ttcgatgcca tcagtgacac atctgacgac    5160
tctgatctaa tcggcatcga ggatagcctg caggagact tagaagagaa aagggcagac    5220
aaagcagtag atgccttggt gaaaaagctg aagaagaacg atggagccat ggggaatac    5280 gaattcaagg cctctcgagc tctagaact atcgtgagtc gtattacgta tatccagaca    5340
tgatgagata cattgatgag tttggacaaa ccgcaactag aatgcagtga aaaaaatgct    5400
ttatttgttg aaatttgtga tgctattgct ttatttggaa ccattataag ctgcaataaa    5460
caagttaaca tcatcaattg cattcatttt atgtttcagg ttcagggggga ggtgtgggag    5520 gctatcc                                                               5527
```

<210> SEQ ID NO 2
<211> LENGTH: 1729
<212> TYPE: PRT
<213> ORGANISM: Pectinophora gossypiella

<400> SEQUENCE: 2

```
Met Ala Gly Asp Ala Cys Ile Leu Val Thr Val Leu Leu Thr Phe Ala
  1               5                  10                  15

Thr Ser Val Phe Gly Gln Glu Thr Thr Ser Ser Arg Cys Tyr Tyr Met
             20                  25                  30

Thr Asp Ala Ile Pro Arg Glu Pro Lys Pro Asp Asp Leu Pro Asp Leu
         35                  40                  45

Glu Trp Thr Gly Gly Trp Thr Asp Trp Pro Leu Ile Pro Ala Glu Pro
     50                  55                  60

Arg Asp Asp Val Cys Ile Asn Gly Trp Tyr Pro Gln Leu Thr Ser Thr
 65                  70                  75                  80

Ser Leu Gly Thr Ile Ile His Met Glu Glu Ile Glu Gly Asp
                 85                  90                  95

Val Ala Ile Ala Lys Leu Asn Tyr Asp Gly Ser Gly Thr Pro Glu Ile
            100                 105                 110

Val Gln Pro Met Val Ile Gly Ser Ser Asn Leu Leu Ser Pro Glu Ile
        115                 120                 125

Arg Asn Glu Asn Gly Ala Trp Tyr Leu Tyr Ile Thr Asn Arg Gln Asp
    130                 135                 140
```

-continued

Tyr Glu Thr Pro Thr Met Arg Arg Tyr Thr Phe Asp Val Arg Val Pro
145                 150                 155                 160

Asp Glu Thr Arg Ala Ala Arg Val Ser Leu Ser Ile Glu Asn Ile Asp
            165                 170                 175

Asp Asn Asp Pro Ile Val Arg Val Leu Asp Ala Cys Gln Val Pro Glu
        180                 185                 190

Leu Gly Glu Pro Arg Leu Thr Asp Cys Val Tyr Gln Val Ser Asp Glu
    195                 200                 205

Asp Gly Arg Leu Ser Ile Glu Pro Met Thr Phe Arg Leu Thr Ser Asp
210                 215                 220

Arg Glu Asp Val Gln Ile Phe Tyr Val Glu Pro Ala His Ile Thr Gly
225                 230                 235                 240

Asp Trp Phe Asn Met Gln Ile Thr Ile Gly Ile Leu Ser Ala Leu Asn
                245                 250                 255

Phe Glu Ser Asn Pro Leu His Ile Phe Gln Ile Thr Ala Leu Asp Ser
            260                 265                 270

Trp Pro Asn Asn His Thr Val Thr Val Met Val Gln Val Gln Asn Val
        275                 280                 285

Glu His Arg Pro Pro Arg Trp Met Glu Ile Phe Ala Val Gln Gln Phe
    290                 295                 300

Asp Glu Met Thr Glu Gln Gln Phe Gln Val Arg Ala Ile Asp Gly Asp
305                 310                 315                 320

Thr Gly Ile Gly Lys Ala Ile His Tyr Thr Leu Glu Thr Asp Glu Glu
                325                 330                 335

Glu Asp Leu Phe Phe Ile Glu Thr Leu Pro Gly Gly His Asp Gly Ala
            340                 345                 350

Ile Phe Ser Thr Ala Met Ile Asp Val Asp Arg Leu Arg Arg Asp Val
        355                 360                 365

Phe Arg Leu Ser Leu Val Ala Tyr Lys Tyr Asp Asn Val Ser Phe Ala
    370                 375                 380

Thr Pro Thr Pro Val Val Ile Ile Val Asn Asp Ile Asn Asn Lys Lys
385                 390                 395                 400

Pro Gln Pro Leu Gln Asp Glu Tyr Thr Ile Ser Ile Met Glu Glu Thr
                405                 410                 415

Pro Leu Ser Leu Asn Phe Ala Glu Leu Phe Gly Phe Tyr Asp Glu Asp
            420                 425                 430

Leu Ile Tyr Ala Gln Ser Leu Val Glu Ile Gln Gly Glu Asn Pro Pro
        435                 440                 445

Gly Val Glu Gln Ala Phe Tyr Ile Ala Pro Thr Ala Gly Phe Gln Asn
    450                 455                 460

Gln Thr Phe Ala Ile Gly Thr Gln Asp His Arg Met Leu Asp Tyr Glu
465                 470                 475                 480

Asp Val Pro Phe Gln Asn Ile Lys Leu Lys Val Ile Ala Thr Asp Arg
                485                 490                 495

Asp Asn Thr Asn Phe Thr Gly Val Ala Glu Val Asn Val Asn Leu Ile
            500                 505                 510

Asn Trp Asn Asp Glu Glu Pro Ile Phe Glu Glu Asp Gln Leu Val Val
        515                 520                 525

Lys Phe Lys Glu Thr Val Pro Lys Asp Tyr His Val Gly Arg Leu Arg
    530                 535                 540

Ala His Asp Arg Asp Ile Gly Asp Ser Val Val His Ser Ile Leu Gly
545                 550                 555                 560

-continued

```
Asn Ala Asn Thr Phe Leu Arg Ile Asp Glu Glu Thr Gly Asp Ile Tyr
                565                 570                 575
Val Ala Ile Asp Asp Ala Phe Asp Tyr His Arg Gln Asn Glu Phe Asn
            580                 585                 590
Ile Gln Val Arg Ala Gln Asp Thr Met Ser Glu Pro Glu Ser Arg His
        595                 600                 605
Thr Ala Ala Gln Leu Val Ile Glu Leu Glu Asp Val Asn Asn Thr
    610                 615                 620
Pro Pro Thr Leu Arg Leu Pro Arg Val Ser Pro Ser Val Glu Glu Asn
625                 630                 635                 640
Val Pro Glu Gly Phe Glu Ile Asn Arg Glu Ile Thr Ala Thr Asp Pro
                645                 650                 655
Asp Thr Thr Ala Tyr Leu Gln Phe Glu Ile Asp Trp Asp Thr Ser Phe
            660                 665                 670
Ala Thr Lys Gln Gly Arg Asp Thr Asn Pro Ile Glu Phe His Gly Cys
        675                 680                 685
Val Asp Ile Glu Thr Ile Phe Pro Asn Pro Ala Asp Thr Arg Glu Ala
    690                 695                 700
Val Gly Arg Val Val Ala Lys Gly Ile Arg His Asn Val Thr Ile His
705                 710                 715                 720
Phe Glu Glu Phe Glu Phe Leu Tyr Leu Thr Val Arg Val Arg Asp Leu
                725                 730                 735
His Thr Asp Asp Gly Arg Asp Tyr Asp Glu Ser Thr Phe Thr Val Ile
            740                 745                 750
Ile Ile Asp Met Asn Asp Asn Trp Pro Ile Trp Ala Ser Gly Phe Leu
        755                 760                 765
Asn Gln Thr Phe Ser Ile Arg Glu Arg Ser Ser Thr Gly Val Val Ile
    770                 775                 780
Gly Ser Val Leu Ala Thr Asp Ile Asp Gly Pro Leu Tyr Asn Gln Val
785                 790                 795                 800
Arg Tyr Thr Ile Ile Pro Gln Glu Asp Thr Pro Glu Gly Leu Val Gln
                805                 810                 815
Ile His Phe Val Thr Gly Gln Ile Thr Val Asp Glu Asn Gly Ala Ile
            820                 825                 830
Asp Ala Asp Ile Pro Pro Arg Trp His Leu Asn Tyr Thr Val Ile Ala
        835                 840                 845
Ser Asp Lys Cys Ser Glu Glu Asn Glu Glu Asn Cys Pro Pro Asp Pro
    850                 855                 860
Val Phe Trp Asp Thr Leu Arg Asp Asn Val Ile Asn Ile Val Asp Ile
865                 870                 875                 880
Asn Asn Lys Val Pro Ala Ala Asp Leu Ser Arg Phe Asn Glu Thr Val
                885                 890                 895
Tyr Ile Tyr Glu Asn Ala Pro Asp Phe Thr Asn Val Val Lys Ile Tyr
            900                 905                 910
Ser Ile Asp Glu Asp Arg Asp Glu Ile Tyr His Thr Val Arg Tyr Gln
        915                 920                 925
Ile Asn Tyr Ala Val Asn Gln Arg Leu Arg Asp Phe Ala Ile Asp
    930                 935                 940
Leu Asp Ser Gly Gln Val Tyr Val Glu Asn Thr Asn Glu Leu Leu
945                 950                 955                 960
Asp Arg Asp Arg Gly Glu Asp Gln His Arg Ile Phe Ile Asn Leu Ile
                965                 970                 975
Asp Asn Phe Tyr Ser Glu Gly Asp Gly Asn Arg Asn Val Asn Thr Thr
```

-continued

```
                980             985             990
Glu Val Leu Val Ile Leu Leu Asp Glu Asn Asp Asn Ala Pro Glu Leu
        995                  1000                1005
Pro Thr Pro Glu Glu Leu Ser Trp Ser Ile Ser Glu Asp Leu Gln Glu
       1010                  1015                1020
Gly Ile Thr Leu Asp Gly Glu Ser Asp Val Ile Tyr Ala Pro Asp Ile
1025                 1030                1035                1040
Asp Lys Glu Asp Thr Pro Asn Ser His Val Gly Tyr Ala Ile Leu Ala
                1045                1050                1055
Met Thr Val Thr Asn Arg Asp Leu Asp Thr Val Pro Arg Leu Leu Asn
            1060                1065                1070
Met Leu Ser Pro Asn Asn Val Thr Gly Phe Leu Gln Thr Ala Met Pro
        1075                1080                1085
Leu Arg Gly Tyr Trp Gly Thr Tyr Asp Ile Ser Val Leu Ala Phe Asp
    1090                1095                1100
His Gly Ile Pro Gln Gln Ile Ser His Glu Val Tyr Glu Leu Glu Ile
1105                1110                1115                1120
Arg Pro Tyr Asn Tyr Asn Pro Pro Gln Phe Val Phe Pro Glu Ser Gly
                1125                1130                1135
Thr Ile Leu Arg Leu Ala Leu Glu Arg Ala Val Val Asn Asn Val Leu
            1140                1145                1150
Ser Leu Val Asn Gly Asp Pro Leu Asp Arg Ile Gln Ala Ile Asp Asp
        1155                1160                1165
Asp Gly Leu Asp Ala Gly Val Val Thr Phe Asp Ile Val Gly Asp Ala
    1170                1175                1180
Asp Ala Ser Asn Tyr Phe Arg Val Asn Asn Asp Gly Asp Ser Phe Gly
1185                1190                1195                1200
Thr Leu Leu Leu Thr Gln Ala Leu Pro Glu Glu Gly Lys Glu Phe Glu
                1205                1210                1215
Val Thr Ile Arg Ala Thr Asp Gly Gly Thr Glu Pro Arg Ser Tyr Ser
            1220                1225                1230
Thr Asp Ser Thr Ile Thr Val Leu Phe Val Pro Thr Leu Gly Asp Pro
        1235                1240                1245
Ile Phe Gln Asp Asn Thr Tyr Ser Val Ala Phe Phe Glu Lys Glu Val
    1250                1255                1260
Gly Leu Thr Glu Arg Phe Ser Leu Pro His Ala Glu Asp Pro Lys Asn
1265                1270                1275                1280
Lys Leu Cys Thr Asp Asp Cys His Asp Ile Tyr Tyr Arg Ile Phe Gly
                1285                1290                1295
Gly Val Asp Tyr Glu Pro Phe Asp Leu Asp Pro Val Thr Asn Val Ile
            1300                1305                1310
Phe Leu Lys Ser Glu Leu Asp Arg Glu Thr Thr Ala Thr His Val Val
        1315                1320                1325
Gln Val Ala Ala Ser Asn Ser Pro Thr Gly Gly Ile Pro Leu Pro
    1330                1335                1340
Gly Ser Leu Leu Thr Val Thr Val Thr Val Arg Glu Ala Asp Pro Arg
1345                1350                1355                1360
Pro Val Phe Glu Gln Arg Leu Tyr Thr Ala Gly Ile Ser Thr Ser Asp
                1365                1370                1375
Asn Ile Asn Arg Glu Leu Leu Thr Val Arg Ala Thr His Ser Glu Asn
            1380                1385                1390
Ala Gln Leu Thr Tyr Thr Ile Glu Asp Gly Ser Met Ala Val Asp Ser
        1395                1400                1405
```

```
Thr Leu Glu Ala Val Lys Asp Ser Ala Phe His Leu Asn Ala Gln Thr
    1410                1415                1420

Gly Val Leu Ile Leu Arg Ile Gln Pro Thr Ala Ser Met Gln Gly Met
1425                1430                1435                1440

Phe Glu Phe Asn Val Ile Ala Thr Asp Pro Asp Lys Thr Asp Thr
                1445                1450                1455

Ala Glu Val Lys Val Tyr Leu Ile Ser Ser Gln Asn Arg Val Ser Phe
                1460                1465                1470

Ile Phe Leu Asn Asp Val Glu Thr Val Glu Ser Asn Arg Asp Phe Ile
            1475                1480                1485

Ala Glu Thr Phe Ser Val Gly Phe Asn Met Thr Cys Asn Ile Asp Gln
            1490                1495                1500

Val Leu Pro Gly Thr Asn Asp Ala Gly Val Ile Gln Glu Ala Met Ala
1505                1510                1515                1520

Glu Val His Ala His Phe Ile Gln Asp Asn Ile Pro Val Ser Ala Asp
                1525                1530                1535

Ser Ile Glu Glu Leu Arg Ser Asp Thr Gln Leu Leu Arg Ser Val Gln
                1540                1545                1550

Gly Val Leu Asn Gln Arg Leu Leu Val Leu Asn Asp Leu Val Thr Gly
                1555                1560                1565

Val Ser Pro Asp Leu Gly Thr Ala Gly Val Gln Ile Thr Ile Tyr Val
    1570                1575                1580

Leu Ala Gly Leu Ser Ala Ile Leu Ala Phe Leu Cys Leu Ile Leu Leu
1585                1590                1595                1600

Ile Thr Phe Ile Val Arg Thr Arg Ala Leu Asn Arg Arg Leu Glu Ala
                1605                1610                1615

Leu Ser Met Thr Lys Tyr Gly Ser Val Asp Ser Gly Leu Asn Arg Val
                1620                1625                1630

Gly Ile Ala Ala Pro Gly Thr Asn Lys His Ala Ile Glu Gly Ser Asn
            1635                1640                1645

Pro Ile Trp Asn Glu Gln Ile Lys Ala Pro Asp Phe Asp Ala Ile Ser
    1650                1655                1660

Asp Thr Ser Asp Asp Ser Asp Leu Ile Gly Ile Glu Asp Ser Leu Gln
1665                1670                1675                1680

Gly Asp Leu Glu Glu Lys Arg Ala Asp Lys Ala Val Asp Ala Leu Val
                1685                1690                1695

Lys Lys Leu Lys Lys Asn Asp Gly Ala Met Gly Glu Tyr Glu Phe Lys
                1700                1705                1710

Ala Ser Arg Ala Ser Arg Thr Ile Val Ser Arg Ile Thr Tyr Ile Gln
        1715                1720                1725

Thr

<210> SEQ ID NO 3
<211> LENGTH: 23
<212> TYPE: DNA
<213> ORGANISM: Artificial sequence
<220> FEATURE:
<223> OTHER INFORMATION: BTR 1209U primer
<220> FEATURE:
<221> NAME/KEY: misc_feature
<222> LOCATION: (3)
<223> OTHER INFORMATION: n = A, G, C, or T
<220> FEATURE:
<221> NAME/KEY: misc_feature
<222> LOCATION: (9)
<223> OTHER INFORMATION: n = A, G, C, or T
<220> FEATURE:
```

```
<221> NAME/KEY: misc_feature
<222> LOCATION: (12)
<223> OTHER INFORMATION: n = A, G, C, or T
<220> FEATURE:
<221> NAME/KEY: misc_feature
<222> LOCATION: (15)
<223> OTHER INFORMATION: n = A, G, C, or T
<220> FEATURE:
<221> NAME/KEY: misc_feature
<222> LOCATION: (21)
<223> OTHER INFORMATION: n = A, G, C, or T

<400> SEQUENCE: 3
canathcgng cncangaygg ngg                                            23

<210> SEQ ID NO 4
<211> LENGTH: 23
<212> TYPE: DNA
<213> ORGANISM: Artificial sequence
<220> FEATURE:
<223> OTHER INFORMATION: BTR 1355U primer

<400> SEQUENCE: 4
ttgtacacsg cwggsatwtc cac                                            23

<210> SEQ ID NO 5
<211> LENGTH: 24
<212> TYPE: DNA
<213> ORGANISM: Artificial sequence
<220> FEATURE:
<223> OTHER INFORMATION: BTR 1486d primer
<220> FEATURE:
<221> NAME/KEY: misc_feature
<222> LOCATION: (1)
<223> OTHER INFORMATION: n = A, G, C, or T
<220> FEATURE:
<221> NAME/KEY: misc_feature
<222> LOCATION: (19)
<223> OTHER INFORMATION: n = A, G, C, or T

<400> SEQUENCE: 5
nacytgrtcr atrttrcang tcat                                           24

<210> SEQ ID NO 6
<211> LENGTH: 24
<212> TYPE: DNA
<213> ORGANISM: Artificial sequence
<220> FEATURE:
<223> OTHER INFORMATION: BTR 1657D primer
<220> FEATURE:
<221> NAME/KEY: misc_feature
<222> LOCATION: (1)
<223> OTHER INFORMATION: n = A, G, C, or T
<220> FEATURE:
<221> NAME/KEY: misc_feature
<222> LOCATION: (7)
<223> OTHER INFORMATION: n = A, G, C, or T
<220> FEATURE:
<221> NAME/KEY: misc_feature
<222> LOCATION: (13)
<223> OTHER INFORMATION: n = A, G, C, or T
<220> FEATURE:
<221> NAME/KEY: misc_feature
<222> LOCATION: (22)
<223> OTHER INFORMATION: n = A, G, C, or T

<400> SEQUENCE: 6
nccdatnagr tcngartcrt tnga                                           24

<210> SEQ ID NO 7
<211> LENGTH: 24
```

```
<212> TYPE: DNA
<213> ORGANISM: Artificial sequence
<220> FEATURE:
<223> OTHER INFORMATION: PBW-BTR GSP-1 primer

<400> SEQUENCE: 7
taggttgtat cctcagtatg agga                                    24

<210> SEQ ID NO 8
<211> LENGTH: 23
<212> TYPE: DNA
<213> ORGANISM: Artificial sequence
<220> FEATURE:
<223> OTHER INFORMATION: PBW-BTR GSP-2 primer

<400> SEQUENCE: 8
ccagagtgga gtccaccgcc ata                                     23

<210> SEQ ID NO 9
<211> LENGTH: 23
<212> TYPE: DNA
<213> ORGANISM: Artificial sequence
<220> FEATURE:
<223> OTHER INFORMATION: PBW-BTR GSP-3 primer

<400> SEQUENCE: 9
ctgagtaagt gttatcttga aag                                     23

<210> SEQ ID NO 10
<211> LENGTH: 23
<212> TYPE: DNA
<213> ORGANISM: Artificial sequence
<220> FEATURE:
<223> OTHER INFORMATION: BTR 1209U primer
<220> FEATURE:
<221> NAME/KEY: misc_feature
<222> LOCATION: (3)
<223> OTHER INFORMATION: n = A, G, C, or T
<220> FEATURE:
<221> NAME/KEY: misc_feature
<222> LOCATION: (9)
<223> OTHER INFORMATION: n = A, G, C, or T
<220> FEATURE:
<221> NAME/KEY: misc_feature
<222> LOCATION: (12)
<223> OTHER INFORMATION: n = A, G, C, or T
<220> FEATURE:
<221> NAME/KEY: misc_feature
<222> LOCATION: (15)
<223> OTHER INFORMATION: n = A, G, C, or T
<220> FEATURE:
<221> NAME/KEY: misc_feature
<222> LOCATION: (21)
<223> OTHER INFORMATION: n = A, G, C, or T

<400> SEQUENCE: 10
canathcgng cncangaygg ngg                                     23

<210> SEQ ID NO 11
<211> LENGTH: 29
<212> TYPE: DNA
<213> ORGANISM: Artificial sequence
<220> FEATURE:
<223> OTHER INFORMATION: PBW-BTR GSP-4 primer

<400> SEQUENCE: 11
gatagcggcc ccaggaacca acaaacagg                               29

<210> SEQ ID NO 12
```

-continued

```
<211> LENGTH: 24
<212> TYPE: DNA
<213> ORGANISM: Artificial sequence
<220> FEATURE:
<223> OTHER INFORMATION: PBW-BTR P2U primer

<400> SEQUENCE: 12
agtgcgagtg ctttgaatct gtga                                              24

<210> SEQ ID NO 13
<211> LENGTH: 25
<212> TYPE: DNA
<213> ORGANISM: Artificial sequence
<220> FEATURE:
<223> OTHER INFORMATION: PBW-BTR P5U primer

<400> SEQUENCE: 13
gtctcttctc accgtcactg tcact                                             25

<210> SEQ ID NO 14
<211> LENGTH: 23
<212> TYPE: DNA
<213> ORGANISM: Artificial sequence
<220> FEATURE:
<223> OTHER INFORMATION: PBW-BTR P6D primer

<400> SEQUENCE: 14
gcatgctggc agtaggttgt atc                                               23

<210> SEQ ID NO 15
<211> LENGTH: 20
<212> TYPE: DNA
<213> ORGANISM: Artificial sequence
<220> FEATURE:
<223> OTHER INFORMATION: (AUAP) primer

<400> SEQUENCE: 15
ggccacgcgt cgactagtac                                                   20

<210> SEQ ID NO 16
<211> LENGTH: 37
<212> TYPE: DNA
<213> ORGANISM: Artificial sequence
<220> FEATURE:
<223> OTHER INFORMATION: (AP) primer

<400> SEQUENCE: 16
ggccacgcgt cgactagtac tttttttttt tttttt                                 37

<210> SEQ ID NO 17
<211> LENGTH: 1715
<212> TYPE: PRT
<213> ORGANISM: B. mori

<400> SEQUENCE: 17
```

Met Gly Val Asp Val Arg Ile Leu Ala Thr Leu Leu Leu Ile Tyr Ala
 1               5                  10                  15

Glu Thr Val Leu Ala Gln Glu Arg Cys Gly Phe Met Val Ala Ile Pro
            20                  25                  30

Arg Pro Pro Arg Pro Asp Leu Pro Glu Leu Asp Phe Glu Gly Gln Thr
        35                  40                  45

Trp Ser Gln Arg Pro Leu Ile Pro Ala Ala Asp Arg Glu Asp Val Cys
    50                  55                  60

Met Asp Gly Tyr His Ala Met Thr Pro Thr Tyr Gly Thr Gln Ile Ile

-continued

```
               65                  70                  75                  80
Tyr Met Glu Glu Ile Glu Gly Glu Val Pro Ile Ala Lys Leu Asn
                    85                  90                  95

Tyr Arg Gly Pro Asn Val Pro Tyr Ile Glu Pro Ala Phe Leu Ser Gly
                100                 105                 110

Ser Phe Asn Leu Leu Val Pro Val Ile Arg Arg Ile Pro Asp Ser Asn
                115                 120                 125

Gly Glu Trp His Leu Ile Ile Thr Gln Arg Gln Asp Tyr Glu Thr Pro
        130                 135                 140

Gly Met Gln Gln Tyr Val Phe Asn Ile Arg Ile Asp Gly Glu Thr Leu
145                 150                 155                 160

Val Ala Gly Val Ser Leu Leu Ile Val Asn Ile Asp Asn Ala Pro
                165                 170                 175

Ile Ile Gln Ala Leu Glu Pro Cys Gln Val Asp Glu Leu Gly Glu Ala
                180                 185                 190

Arg Leu Thr Glu Cys Val Tyr Val Thr Asp Ala Asp Gly Arg Ile
            195                 200                 205

Ser Thr Gln Phe Met Gln Phe Arg Ile Asp Ser Asp Arg Gly Asp Asp
        210                 215                 220

Lys Ile Phe Tyr Ile Gln Gly Ala Asn Ile Pro Gly Glu Trp Ile Arg
225                 230                 235                 240

Met Thr Met Thr Val Gly Ile Asn Glu Pro Leu Asn Phe Glu Thr Asn
                245                 250                 255

Pro Leu His Ile Phe Ser Val Thr Ala Leu Asp Ser Leu Pro Asn Thr
                260                 265                 270

His Thr Val Thr Leu Met Val Gln Val Glu Asn Val Glu His Arg Pro
            275                 280                 285

Pro Arg Trp Val Glu Ile Phe Ala Val Gln Gln Phe Asp Glu Lys Thr
        290                 295                 300

Ala Gln Ser Phe Pro Val Arg Ala Ile Asp Gly Asp Thr Gly Ile Asn
305                 310                 315                 320

Lys Pro Ile His Tyr Arg Leu Glu Thr Ala Glu Glu Asp Thr Phe Phe
                325                 330                 335

His Ile Arg Thr Ile Glu Gly Gly Arg Ser Gly Ala Ile Leu Tyr Val
                340                 345                 350

Asp Pro Ile Asp Arg Asp Thr Leu Gln Arg Glu Val Phe Gln Leu Ser
            355                 360                 365

Ile Ile Ala Tyr Lys Tyr Asp Asn Glu Ser Ser Ala Thr Ala Ala Asn
        370                 375                 380

Val Val Ile Ile Val Asn Asp Ile Asn Asp Gln Arg Pro Glu Pro Leu
385                 390                 395                 400

Phe Lys Glu Tyr Arg Leu Asn Ile Met Glu Glu Thr Ala Leu Thr Leu
                405                 410                 415

Asn Phe Asp Gln Glu Phe Gly Phe His Asp Arg Asp Leu Gly Gln Asn
                420                 425                 430

Ala Gln Tyr Thr Val Arg Leu Glu Ser Asp Tyr Pro Ala Asp Ala Ala
            435                 440                 445

Lys Ala Phe Tyr Ile Ala Pro Glu Val Gly Tyr Gln Arg Gln Thr Phe
        450                 455                 460

Ile Met Gly Thr Ala Asn His Lys Met Leu Asp Tyr Glu Val Pro Glu
465                 470                 475                 480

Phe Gln Arg Ile Arg Leu Arg Val Ile Ala Thr Asp Met Asp Asn Glu
                485                 490                 495
```

-continued

Glu His Val Gly Val Ala Tyr Val Tyr Ile Asn Leu Ile Asn Trp Asn
            500                 505                 510

Asp Glu Glu Pro Ile Phe Glu His Ser Val Gln Asn Val Ser Phe Lys
            515                 520                 525

Glu Thr Glu Gly Lys Gly Phe Phe Val Ala Asn Val Arg Ala His Asp
            530                 535                 540

Arg Asp Ile Asp Asp Arg Val Glu His Thr Leu Met Gly Asn Ala Asn
545                 550                 555                 560

Asn Tyr Leu Ser Ile Asp Lys Asp Thr Gly Asp Ile His Val Thr Gln
                565                 570                 575

Asp Asp Phe Phe Asp Tyr His Arg Gln Ser Glu Leu Phe Val Gln Val
            580                 585                 590

Arg Ala Asp Asp Thr Leu Gly Glu Pro Phe His Thr Ala Thr Ser Gln
            595                 600                 605

Leu Leu Ile His Glu Glu Asp Ile Asn Asn Thr Pro Pro Thr Leu Arg
            610                 615                 620

Leu Pro Arg Gly Ser Pro Asn Val Glu Glu Asn Val Pro Glu Gly Tyr
625                 630                 635                 640

Ile Ile Thr Ser Glu Ile Arg Ala Thr Asp Pro Asp Thr Thr Ala Glu
                645                 650                 655

Leu Arg Phe Glu Ile Asp Trp Thr Thr Ser Tyr Ala Thr Lys Gln Gly
            660                 665                 670

Arg Glu Ala Asn Pro Ile Glu Phe His Asn Cys Val Glu Ile Glu Thr
            675                 680                 685

Ile Tyr Pro Ala Ile Asn Asn Arg Gly Ser Ala Ile Gly Arg Leu Val
            690                 695                 700

Val Lys Lys Ile Arg Glu Asn Val Thr Ile Asp Tyr Glu Glu Phe Glu
705                 710                 715                 720

Met Leu Tyr Leu Thr Val Arg Val Arg Asp Leu Asn Thr Val Ile Gly
                725                 730                 735

Asp Asp Tyr Asp Glu Ser Thr Phe Thr Ile Thr Ile Asp Met Asn
            740                 745                 750

Asp Asn Pro Pro Ile Trp Val Pro Gly Thr Leu Glu Gln Ser Leu Arg
            755                 760                 765

Val Arg Glu Met Ser Asp Ala Gly Val Val Ile Gly Thr Leu Thr Ala
            770                 775                 780

Thr Asp Ile Asp Gly Pro Leu Tyr Asn Gln Val Arg Tyr Thr Met Lys
785                 790                 795                 800

Ala Asn Glu Gly Thr Pro Glu Asn Leu Leu Met Glx Asp Phe Tyr Thr
                805                 810                 815

Gly Gln Ile Thr Val Lys Thr Ser Gly Ala Ile Asp Ala Asp Val Pro
            820                 825                 830

Arg Arg Tyr Asn Leu Tyr Tyr Thr Val Ala Thr Asp Arg Cys Tyr
            835                 840                 845

Ala Glu Asp Pro Asp Asp Cys Pro Asp Asp Pro Thr Tyr Trp Glu Thr
            850                 855                 860

Pro Gly Gln Val Val Ile Gln Ile Ile Asp Thr Asn Asn Lys Ile Pro
865                 870                 875                 880

Gln Pro Glu Thr Asp Gln Phe Lys Ala Val Val Tyr Ile Tyr Glu Asp
                885                 890                 895

Ala Val Ser Gly Asp Glu Val Val Lys Val Ile Gly Ser Asp Leu Asp
            900                 905                 910

-continued

```
Arg Asp Asp Ile Tyr His Thr Ile Arg Tyr Gln Ile Asn Tyr Ala Val
        915                 920                 925

Asn Pro Arg Leu Arg Asp Phe Phe Ala Val Asp Pro Asp Thr Gly Arg
        930                 935                 940

Val Tyr Val Tyr Tyr Thr Thr Asp Glu Val Leu Asp Arg Asp Gly Asp
945                 950                 955                 960

Glu Pro Gln His Arg Ile Phe Phe Asn Leu Ile Asp Asn Phe Phe Gln
                965                 970                 975

Gln Gly Asp Gly Asn Arg Asn Gln Asn Asp Ala Glu Val Leu Val Val
                980                 985                 990

Leu Leu Asp Val Asn Asp Asn Ala Pro Glu Leu Pro Glu Pro Asp Glu
        995                 1000                1005

Leu Ser Trp Ser Val Ser Glu Ser Leu Thr Lys Gly Thr Arg Leu Gln
        1010                1015                1020

Pro His Ile Tyr Ala Pro Asp Arg Asp Glu Pro Asp Thr Asp Asn Ser
1025                1030                1035                1040

Arg Val Gly Tyr Ala Ile Ile Ser Leu Thr Ile Ala Asn Arg Glu Ile
                1045                1050                1055

Glu Val Pro Glu Leu Phe Thr Met Ile Gln Ile Gln Asn Val Thr Gly
        1060                1065                1070

Glu Leu Glu Thr Ala Met Asp Leu Arg Gly Tyr Trp Gly Thr Tyr Ala
        1075                1080                1085

Ile His Ile Lys Ala Tyr Asp His Gly Ile Pro Gln Gln Met Ser Asn
        1090                1095                1100

Glu Thr Tyr Glu Leu Val Ile Arg Pro Tyr Asn Phe His Ala Pro Val
1105                1110                1115                1120

Phe Val Phe Pro Lys His Gly Ala Thr Leu Arg Leu Ala Arg Glu Arg
                1125                1130                1135

Ala Val Val Asn Gly Leu Leu Ala Thr Val Asp Gly Glu Phe Leu Asn
                1140                1145                1150

Arg Ile Val Ala Thr Asp Glu Asp Gly Leu His Ala Gly Gln Val Ala
        1155                1160                1165

Phe Glu Val Val Gly Asp Thr Glu Ala Val Asp Tyr Phe His Ile Val
        1170                1175                1180

Asn Asp Gly Glu Asn Ser Gly Thr Leu Met Leu Lys Gln Leu Phe Pro
1185                1190                1195                1200

Glu Asp Ile Arg Glu Phe Glu Val Thr Ile Arg Ala Thr Asp Gly Gly
                1205                1210                1215

Thr Glu Pro Arg Pro Leu Ser Thr Asp Cys Thr Phe Ser Val Val Phe
        1220                1225                1230

Val Pro Ile Gln Gly Glu Pro Ile Phe Pro Thr Ser Thr His Thr Val
        1235                1240                1245

Ala Phe Ile Glu Lys Glu Ala Gly Leu Leu Glu Arg His Glu Leu Pro
        1250                1255                1260

Arg Ala Glu Asp Arg Lys Asn His Leu Cys Ser Asp Cys His Asn
1265                1270                1275                1280

Ile Tyr Tyr Arg Ile Ile Asp Gly Asn Asn Asp Gly His Phe Gly Leu
                1285                1290                1295

Asp Glu Thr Thr Asn Val Leu Phe Leu Val Lys Glu Leu Asp Arg Ser
        1300                1305                1310

Val Ser Glu Thr Tyr Thr Leu Thr Ile Ala Ala Ser Asn Ser Pro Thr
        1315                1320                1325

Gly Gly Ile Ala Leu Thr Ser Thr Ile Thr Ile Thr Val Asn Val Arg
```

```
                    1330                1335                1340
Glu Ala Asp Pro Gln Pro Tyr Phe Val Arg Asp Leu Tyr Thr Ala Gly
1345                1350                1355                1360

Ile Ser Thr Ser Asp Ser Ile Asn Arg Glu Leu Leu Ile Leu Gln Ala
            1365                1370                1375

Thr His Ser Glu Asn Ala Pro Ile Ile Tyr Thr Ile Asp Trp Ser Thr
        1380                1385                1390

Met Val Thr Asp Pro Thr Leu Ala Ser Val Arg Glu Thr Ala Phe Ile
        1395                1400                1405

Leu Asn Pro His Thr Gly Val Leu Thr Leu Asn Ile Gln Pro Thr Ala
    1410                1415                1420

Ser Met His Gly Met Phe Glu Phe Gln Val Val Ala Thr Asp Pro Ala
1425                1430                1435                1440

Gly Tyr Ser Asp Arg Ala Asn Val Lys Ile Tyr Leu Ile Ser Thr Arg
            1445                1450                1455

Asn Arg Val Phe Phe Leu Phe Val Asn Thr Leu Glu Gln Val Glu Gln
        1460                1465                1470

Asn Thr Asp Phe Ile Ala Gln Thr Phe Ser Ala Gly Phe Glu Met Thr
    1475                1480                1485

Cys Asn Ile Asp Gln Val Val Pro Ala Thr Asp Ala Ser Gly Val Ile
    1490                1495                1500

Met Asn Gly Ile Thr Glu Val Arg Gly His Phe Ile Arg Asp Asn Val
1505                1510                1515                1520

Pro Val Pro Ala Asp Glu Ile Glu Thr Leu Arg Gly Asp Met Val Leu
            1525                1530                1535

Leu Thr Ala Ile Gln Ser Thr Leu Ala Thr Arg Leu Leu Val Leu Arg
        1540                1545                1550

Asp Leu Phe Thr Asp Thr Ser Pro Ala Pro Asp Ala Gly Ser Ala Ala
    1555                1560                1565

Val Leu Tyr Ala Leu Ala Val Leu Ser Ala Leu Leu Ala Leu Cys
    1570                1575                1580

Leu Leu Leu Leu Val Ile Phe Ile Ile Arg Thr Lys Lys Leu Asn Arg
1585                1590                1595                1600

Arg Leu Glu Ala Leu Thr Val Lys Lys Tyr Gly Ser Val Asp Ser Gly
            1605                1610                1615

Leu Asn Arg Val Gly Ile Ala Ala Pro Gly Thr Asn Lys His Ala Val
        1620                1625                1630

Glu Gly Ser Asn Pro Ile Trp Asn Glu Thr Ile Lys Ala Pro Asp Phe
    1635                1640                1645

Asp Ser Met Ser Asp Ala Ser Asn Asp Ser Asp Leu Ile Gly Ile Glu
    1650                1655                1660

Asp Leu Pro His Phe Gly Glu Asn Asn Tyr Phe Pro Arg Asp Val Asp
1665                1670                1675                1680

Glu Phe Lys Thr Asp Lys Pro Glu Asp Ile Val Ala Thr His Asn Asn
            1685                1690                1695

Asn Phe Gly Phe Lys Ser Thr Pro Phe Ser Pro Glu Phe Ala Asn Gln
        1700                1705                1710

Phe Gln Lys
        1715

<210> SEQ ID NO 18
<211> LENGTH: 1717
<212> TYPE: PRT
<213> ORGANISM: Tobacco hornworm
```

-continued

<400> SEQUENCE: 18

```
Met Ala Val Asp Val Arg Ile Ala Ala Phe Leu Leu Val Phe Ile Ala
1               5                   10                  15

Pro Ala Val Leu Ala Gln Glu Arg Cys Gly Tyr Met Thr Ala Ile Pro
            20                  25                  30

Arg Leu Pro Arg Pro Asp Asn Leu Pro Val Leu Asn Phe Glu Gly Gln
        35                  40                  45

Thr Trp Ser Gln Arg Pro Leu Leu Pro Ala Pro Glu Arg Asp Asp Leu
    50                  55                  60

Cys Met Asp Ala Tyr His Val Ile Thr Ala Asn Leu Gly Thr Gln Val
65                  70                  75                  80

Ile Tyr Met Asp Glu Glu Ile Glu Asp Glu Ile Thr Ile Ala Ile Leu
                85                  90                  95

Asn Tyr Asn Gly Pro Ser Thr Pro Phe Ile Glu Leu Pro Phe Leu Ser
            100                 105                 110

Gly Ser Tyr Asn Leu Leu Met Pro Val Ile Arg Arg Val Asp Asn Gly
        115                 120                 125

Glu Trp His Leu Ile Ile Thr Gln Arg Gln His Tyr Glu Leu Pro Gly
    130                 135                 140

Met Gln Gln Tyr Met Phe Asn Val Arg Val Asp Gly Gln Ser Leu Val
145                 150                 155                 160

Ala Gly Val Ser Leu Ala Ile Val Asn Ile Asp Asp Asn Ala Pro Ile
                165                 170                 175

Ile Gln Asn Phe Glu Pro Cys Arg Val Pro Glu Leu Gly Glu Pro Gly
            180                 185                 190

Leu Thr Glu Cys Thr Tyr Gln Val Ser Asp Ala Asp Gly Arg Ile Ser
        195                 200                 205

Thr Glu Phe Met Thr Phe Arg Ile Asp Ser Val Arg Gly Asp Glu Glu
    210                 215                 220

Thr Phe Tyr Ile Glu Arg Thr Asn Ile Pro Asn Gln Trp Met Trp Leu
225                 230                 235                 240

Asn Met Thr Ile Gly Val Asn Thr Ser Leu Asn Phe Val Thr Ser Pro
                245                 250                 255

Leu His Ile Phe Ser Val Thr Ala Leu Asp Ser Leu Pro Asn Thr His
            260                 265                 270

Thr Val Thr Met Met Val Gln Val Ala Asn Val Asn Ser Arg Pro Pro
        275                 280                 285

Arg Trp Leu Glu Ile Phe Ala Val Gln Gln Phe Glu Glu Lys Ser Tyr
    290                 295                 300

Gln Asn Phe Thr Val Arg Ala Ile Asp Gly Asp Thr Glu Ile Asn Met
305                 310                 315                 320

Pro Ile Asn Tyr Arg Leu Ile Thr Asn Glu Glu Asp Thr Phe Phe Ser
                325                 330                 335

Ile Glu Ala Leu Pro Gly Gly Lys Ser Gly Ala Val Phe Leu Val Ser
            340                 345                 350

Pro Ile Asp Arg Asp Thr Leu Gln Arg Glu Val Phe Pro Leu Thr Ile
        355                 360                 365

Val Ala Tyr Lys Tyr Asp Glu Glu Ala Phe Ser Thr Ser Thr Asn Val
    370                 375                 380

Val Ile Ile Val Thr Asp Ile Asn Asp Gln Arg Pro Glu Pro Ile His
385                 390                 395                 400

Lys Glu Tyr Arg Leu Ala Ile Met Glu Glu Thr Pro Leu Thr Leu Asn
```

-continued

```
              405                 410                 415
Phe Asp Lys Glu Phe Gly Phe His Asp Lys Asp Leu Gly Gln Asn Ala
            420                 425                 430
Gln Tyr Thr Val Arg Leu Glu Ser Val Asp Pro Gly Ala Ala Glu
        435                 440                 445
Ala Phe Tyr Ile Ala Pro Glu Val Gly Tyr Gln Arg Gln Thr Phe Ile
        450                 455                 460
Met Gly Thr Leu Asn His Ser Met Leu Asp Tyr Glu Val Pro Glu Phe
465                 470                 475                 480
Gln Ser Ile Thr Ile Arg Val Val Ala Thr Asp Asn Asn Asp Thr Arg
                485                 490                 495
His Val Gly Val Ala Leu Val His Ile Asp Leu Ile Asn Trp Asn Asp
            500                 505                 510
Glu Gln Pro Ile Phe Glu His Ala Val Gln Thr Val Thr Phe Asp Glu
        515                 520                 525
Thr Glu Gly Glu Gly Phe Val Ala Lys Ala Val Ala His Asp Arg
        530                 535                 540
Asp Ile Gly Asp Val Val Glu His Thr Leu Leu Gly Asn Ala Val Asn
545                 550                 555                 560
Phe Leu Thr Ile Asp Lys Leu Thr Gly Asp Ile Arg Val Ser Ala Asn
                565                 570                 575
Asp Ser Phe Asn Tyr His Arg Glu Ser Glu Leu Phe Val Gln Val Arg
            580                 585                 590
Ala Thr Asp Thr Leu Gly Glu Pro Phe His Thr Ala Thr Ser Gln Leu
        595                 600                 605
Val Ile Arg Leu Asn Asp Ile Asn Asn Thr Pro Pro Thr Leu Arg Leu
        610                 615                 620
Pro Arg Gly Ser Pro Gln Val Glu Glu Asn Val Pro Asp Gly His Val
625                 630                 635                 640
Ile Thr Gln Glu Leu Arg Ala Thr Asp Pro Asp Thr Thr Ala Asp Leu
                645                 650                 655
Arg Phe Glu Ile Asn Trp Asp Thr Ser Phe Ala Thr Lys Gln Gly Arg
            660                 665                 670
Gln Ala Asn Pro Asp Glu Phe Arg Asn Cys Val Glu Ile Glu Thr Ile
        675                 680                 685
Phe Pro Glu Ile Asn Asn Arg Gly Leu Ala Ile Gly Arg Val Val Ala
        690                 695                 700
Arg Glu Ile Arg His Asn Val Thr Ile Asp Tyr Glu Glu Phe Glu Val
705                 710                 715                 720
Leu Ser Leu Thr Val Arg Val Arg Asp Leu Asn Thr Val Tyr Gly Asp
                725                 730                 735
Asp Tyr Asp Glu Ser Met Leu Thr Ile Thr Ile Asp Met Asn Asp
            740                 745                 750
Asn Ala Pro Val Trp Val Gly Thr Leu Glu Gln Asn Phe Arg Val
        755                 760                 765
Arg Glu Met Ser Ala Gly Gly Leu Val Val Gly Ser Val Arg Ala Asp
        770                 775                 780
Asp Ile Asp Gly Pro Leu Tyr Asn Gln Val Arg Tyr Thr Ile Phe Pro
785                 790                 795                 800
Arg Glu Asp Thr Asp Lys Asp Leu Ile Met Ile Asp Phe Leu Thr Gly
                805                 810                 815
Gln Ile Ser Val Asn Thr Ser Gly Ala Ile Asp Ala Asp Thr Pro Pro
            820                 825                 830
```

-continued

```
Arg Phe His Leu Tyr Tyr Thr Val Ala Ser Asp Arg Cys Ser Thr
        835                 840                 845

Glu Asp Pro Ala Asp Cys Pro Pro Asp Pro Thr Tyr Trp Glu Thr Glu
    850                 855                 860

Gly Asn Ile Thr Ile His Ile Thr Asp Thr Asn Asn Lys Val Pro Gln
865                 870                 875                 880

Ala Glu Thr Thr Lys Phe Asp Thr Val Val Tyr Ile Tyr Glu Asn Ala
                885                 890                 895

Thr His Leu Asp Glu Val Val Thr Leu Ile Ala Ser Asp Leu Asp Arg
                900                 905                 910

Asp Glu Ile Tyr His Thr Val Ser Tyr Val Ile Asn Tyr Ala Val
                915                 920                 925

Asn Pro Arg Leu Met Asn Phe Phe Ser Val Asn Arg Glu Thr Gly Leu
    930                 935                 940

Val Tyr Val Asp Tyr Glu Thr Gln Gly Ser Gly Glu Val Leu Asp Arg
945                 950                 955                 960

Asp Gly Asp Glu Pro Thr His Arg Ile Phe Phe Asn Leu Ile Asp Asn
                965                 970                 975

Phe Met Gly Glu Gly Glu Gly Asn Arg Asn Gln Asn Asp Thr Glu Val
                980                 985                 990

Leu Val Ile Leu Leu Asp Val Asn Asp Asn Ala Pro Glu Leu Pro Pro
            995                 1000                1005

Pro Ser Glu Leu Ser Trp Thr Ile Ser Glu Asn Leu Lys Gln Gly Val
    1010                1015                1020

Arg Leu Glu Pro His Ile Phe Ala Pro Asp Arg Asp Glu Pro Asp Thr
1025                1030                1035                1040

Asp Asn Ser Arg Val Gly Tyr Glu Ile Leu Asn Leu Ser Thr Glu Arg
                1045                1050                1055

Asp Ile Glu Val Pro Glu Leu Phe Val Met Ile Gln Ile Ala Asn Val
                1060                1065                1070

Thr Gly Glu Leu Glu Thr Ala Met Asp Leu Lys Gly Tyr Trp Gly Thr
                1075                1080                1085

Tyr Ala Ile His Ile Arg Ala Phe Asp His Gly Ile Pro Gln Met Ser
    1090                1095                1100

Met Asn Glu Thr Tyr Glu Leu Ile Ile His Pro Phe Asn Tyr Tyr Ala
1105                1110                1115                1120

Pro Glu Phe Val Phe Pro Thr Asn Asp Ala Val Ile Arg Leu Ala Arg
                1125                1130                1135

Glu Arg Ala Val Ile Asn Gly Val Leu Ala Thr Val Asn Gly Glu Phe
                1140                1145                1150

Leu Glu Arg Ile Ser Ala Thr Asp Pro Asp Gly Leu His Ala Gly Val
    1155                1160                1165

Val Thr Phe Gln Val Val Gly Asp Glu Glu Ser Gln Arg Tyr Phe Gln
    1170                1175                1180

Val Val Asn Asp Gly Glu Asn Leu Gly Ser Leu Arg Leu Leu Gln Ala
1185                1190                1195                1200

Val Pro Glu Glu Ile Arg Glu Phe Arg Ile Thr Ile Arg Ala Thr Asp
                1205                1210                1215

Gln Gly Thr Asp Pro Gly Pro Leu Ser Thr Asp Met Thr Phe Arg Val
                1220                1225                1230

Val Phe Val Pro Thr Gln Gly Glu Pro Arg Phe Ala Ser Ser Glu His
                1235                1240                1245
```

```
Ala Val Ala Phe Ile Glu Lys Ser Ala Gly Met Glu Ser His Gln
    1250                1255                1260

Leu Pro Leu Ala Gln Asp Ile Lys Asn His Leu Cys Glu Asp Cys
1265                1270                1275                1280

His Ser Ile Tyr Tyr Arg Ile Ile Asp Gly Asn Ser Glu Gly His Phe
            1285                1290                1295

Gly Leu Asp Pro Val Arg Asn Arg Leu Phe Leu Lys Lys Glu Leu Ile
            1300                1305                1310

Arg Glu Gln Ser Ala Ser His Thr Leu Gln Val Ala Ala Ser Asn Ser
            1315                1320                1325

Pro Asp Gly Gly Ile Pro Leu Pro Ala Ser Ile Leu Thr Val Thr Val
    1330                1335                1340

Thr Val Arg Glu Ala Asp Pro Arg Pro Val Phe Val Arg Glu Leu Tyr
1345                1350                1355                1360

Thr Ala Gly Ile Ser Thr Ala Asp Ser Ile Gly Arg Glu Leu Leu Arg
            1365                1370                1375

Leu His Ala Thr Gln Ser Glu Gly Ser Ala Ile Thr Tyr Ala Ile Asp
            1380                1385                1390

Tyr Asp Thr Met Val Val Asp Pro Ser Leu Glu Ala Val Arg Gln Ser
            1395                1400                1405

Ala Phe Val Leu Asn Ala Gln Thr Gly Val Leu Thr Leu Asn Ile Gln
            1410                1415                1420

Pro Thr Ala Thr Met His Gly Leu Phe Lys Phe Glu Val Thr Ala Thr
1425                1430                1435                1440

Asp Thr Ala Gly Ala Gln Asp Arg Thr Asp Val Thr Val Tyr Val Val
            1445                1450                1455

Ser Ser Gln Asn Arg Val Tyr Phe Val Phe Val Asn Thr Leu Gln Gln
            1460                1465                1470

Val Glu Asp Asn Arg Asp Phe Ile Ala Asp Thr Phe Ser Ala Gly Phe
            1475                1480                1485

Asn Met Thr Cys Asn Ile Asp Gln Val Val Pro Ala Asn Asp Pro Val
            1490                1495                1500

Thr Gly Val Ala Leu Glu His Ser Thr Gln Met Arg Gly His Phe Ile
1505                1510                1515                1520

Arg Asp Asn Val Pro Val Leu Ala Asp Glu Ile Glu Gln Ile Arg Ser
            1525                1530                1535

Asp Leu Val Leu Leu Ser Ser Ile Gln Thr Thr Leu Ala Ala Arg Ser
            1540                1545                1550

Leu Val Leu Asp Leu Leu Thr Asn Ser Ser Pro Asp Ser Ala Pro Asp
            1555                1560                1565

Ser Ser Leu Thr Val Tyr Val Leu Ala Ser Leu Ser Ala Val Leu Gly
            1570                1575                1580

Phe Met Cys Leu Val Leu Leu Leu Thr Phe Ile Ile Arg Thr Arg Ala
1585                1590                1595                1600

Leu Asn Arg Arg Leu Glu Ala Leu Ser Met Thr Lys Tyr Gly Ser Leu
            1605                1610                1615

Asp Ser Gly Leu Asn Arg Ala Gly Ile Ala Ala Pro Gly Thr Asn Lys
            1620                1625                1630

His Thr Val Glu Gly Ser Asn Pro Ile Phe Asn Glu Ala Ile Lys Thr
            1635                1640                1645

Pro Asp Leu Asp Ala Ile Ser Glu Gly Ser Asn Asp Ser Asp Leu Ile
            1650                1655                1660

Gly Ile Glu Asp Leu Pro His Phe Gly Asn Val Phe Met Asp Pro Glu
```

-continued

```
       1665                1670                1675                1680
Val Asn Glu Lys Ala Asn Gly Tyr Pro Glu Val Ala Asn His Asn Asn
                   1685                1690                1695

Asn Phe Ala Phe Asn Pro Thr Pro Phe Ser Pro Glu Phe Val Asn Gly
               1700                1705                1710

Gln Phe Arg Lys Ile
            1715
```

PECTINOPHORA GOSSYPIELLA (PINK BOLLWORM) BACILLUS THURINGIENSIS TOXIN RECEPTOR BT-R$_2$

CROSS-REFERENCES TO RELATED APPLICATIONS

This application is a divisional of U.S. Ser. No. 09/696,115 filed 24 Oct. 2000, now U.S. Pat. No. 6,660,497, which claims the benefit of U.S. Provisional Application No. 60/161,564, filed Oct. 26, 1999. The contents of this application are incorporated herein by reference.

TECHNICAL FIELD OF THE INVENTION

This invention generally relates to receptors for *Bacillus thuringiensis* (BT) toxin and thus to pesticides able to bind the receptor, and to ameliorating pesticide resistance. In particular, the invention relates to recombinant DNA and expression systems for a novel receptor and receptor elements from *Pectinophora gossypiella*, the pink bollworm.

BACKGROUND OF THE INVENTION

Without limiting the scope of the invention, its background is described in connection with uses of *Bacillus thuringiensis* toxins as cotton insect biocidal agents, as an example. Cotton insect pests reduced yields by almost 10% across the US in 1998. Insect damage reduced the overall cotton yield by more than 1.7 million bales and produced a financial loss of about $1.224 billion. One group in particular, the bollworm/budworm complex was the most damaging causing a 2.7% loss. The pink bollworm, *Pectinophora gossypiella* Saunders ("PBW"), is a lepidopteran insect that causes severe damage to cotton and is the most destructive pest of cotton worldwide.

*Bacillus thuringiensis* is a gram positive, sporeforming bacterium that forms a parasporal crystal which contains insecticidal toxins (Bulla et al., *Crit. Rev. Microbiol.* (1980) 8: 147–204; Höfte and Whiteley, *Microbiol. Rev.* (1989) 53: 242. The effect of the toxin is mediated through binding to specific receptors on the apical brush border of the midgut microvillae (BBMV) of susceptible insects.

Biological control of cotton pests using *B. thuringiensis* formulations and transgenic plants has been in use for a number of years and is growing rapidly. Recently, transgenic cotton plants carrying the toxin genes of BT have been developed and sold commercially. Such transgenic plants have a high degree of resistance to the pink bollworm (Schnepf et al., *Microbiol. Mol. Biol. Rev.* (1998) 62: 775). However, the introduction of any new insecticide into a pest management program immediately initiates a selection process for individuals that are resistant to the pesticide. As the use of transgenic crops expressing BT toxin increases, insect resistance is expected to become more widespread. Increased tolerance for BT toxins in several species of insects has been reported by several investigators while laboratory selection experiments have shown that the use of BT toxin formulations and transgenic plants can provoke the development of resistance in the pink bollworm (Bartlett, et al., *Beltwide Cotton Conference* (1995) 2: 766).

Concerns that BT toxin formulations or transgenic plants expressing the toxin genes may evoke emergence of either resistant or tolerant strains of insects has made the search for a better understanding of the interaction between the BT toxin proteins and their respective insect receptors a matter of considerable economic importance.

In U.S. Pat. No. 5,693,491, the present inventors disclosed the purification and cDNA cloning of a *B. thuringiensis* toxin receptor BT-R$_1$ from larvae of the tobacco hornworm *Manduca sexta* (*M. Sexta*). Recently, two BT toxin receptors have been identified, purified and cloned from the silkworm, *Bombyx mori* (Nagamatsu et al., *Biosci. Biotechnol. Biochem.* (1998) 62: 727).

Heretofore in this field, there has been no structural information concerning the structure and function of BT toxin receptor of the major cotton insect pest, *P. gossypiella*. Furthermore, to the inventors' knowledge, the minimum binding fragment encoding a consensus binding domain for BT toxin on the BT receptor has not yet been identified. Isolation of the minimum binding fragment could permit cloning and structural characterization of important yet uncharacterized BT toxin receptors from other insects of worldwide economic importance such as *P. gossypiella*.

SUMMARY OF THE INVENTION

The present invention provides information and materials for isolation and expression of novel BT crystal toxin receptors, herein referred to as Cry toxin receptors. Generally, the invention provides structural and functional characterization of a novel lepidopteran BT toxin receptor, herein referred to as BT-R$_2$.

A cDNA that encodes an alternative glycoprotein receptor from the pink bollworm that binds specifically to a *B. thuringiensis* toxin has been cloned, sequenced and characterized. The BT-R$_2$ cDNA permits the analysis of receptors in pink bollworm and other insects and organisms that affect crop growth and development, as well as the design of assays for the cytotoxicity and binding affinity of potential pesticides. The clone and other methods described herein, permit the manipulation of natural and/or introduced homologous receptors and, thus, to specifically destroy organisms, tissues and/or cells of the target host, including insects resistant to toxins of *B. thuringiensis*.

The invention further provides purified and cloned cDNA encoding a 200 kD receptor for the Cry1A toxins of the pink bollworm, *P. gossypiella*. An advantage of this invention is the identification of the minimum binding fragment encoding the toxin binding domain on the BT toxin receptor. Another advantage of this invention is the provision of methodologies for cloning and structural characterization of presently unknown BT receptors. Furthermore, this invention provides methods and materials for identification and design of effective toxin binding receptors for use in combating emergence of toxin resistance. Also, this invention may be used to generate transgenic organisms expressing toxin receptors.

BRIEF DESCRIPTION OF THE DRAWINGS

A more complete understanding of the method and apparatus of the present invention may be obtained by reference to the following Detailed Description when taken in conjunction with the accompanying Drawings wherein:

FIGS, 1A–B show the nucleotide sequence cDNA encoding the BT-R$_2$ protein from *P. gossypiella* (SEQ ID NO:1);

FIGS. 2A and 2B show the amino acid sequence of BT-R2 protein from *P. gossypiella* (SEQ ID NO: 2). Arrows indicate the start site of the putative cadherin domains CR1–CR12, SIG=signal sequence (double underline); MPD=membrane proximal domain; CYT=cytoplasmic region. The transmembrane region is underlined and bold. The leucine zipper motif LZ is underlined. Ñ residues denote putative N-glycosylation sites. The minimum binding fragment MBF (aa 1269–1367) is also double underlined;

FIGS. 5A–C illustrate an alignment of the silk worm (top SEQ ID NO:17), the tobacco hornworm (middle SEQ ID NO:18), and the pink bollworm (bottom SEQ ID NO:2) Cry toxin receptors. Perfectly conserved residues are boxed.

DETAILED DESCRIPTION OF THE PRESENTLY PREFERRED EXEMPLARY EMBODIMENTS

Figure 3A:
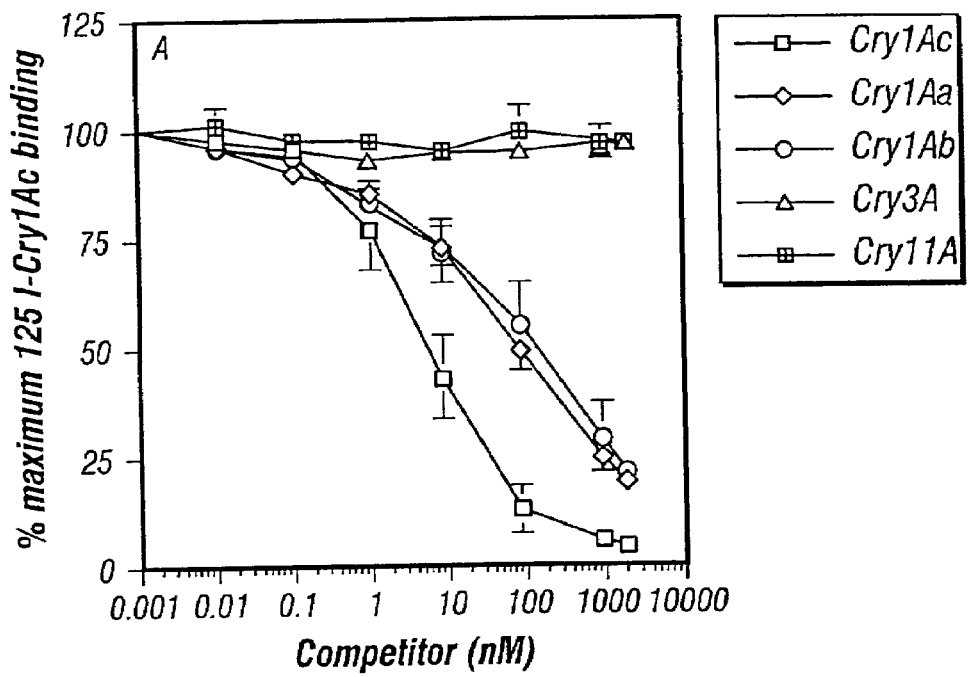
FIG. 3A is a graph showing the binding results of Cry1A toxins on *P. gossypiella* larvae brush border membrane vesicles prepared from midgut epithelial cells.

The present invention will now be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Abbreviations and Definitions

The following abbreviations are used throughout this application: bp—base pairs; BT—*Bacillus thuringiensis* or *B. thuringiensis;* BT-R$_x$—BT toxin receptor of type x; BBMV—brush border of the membrane vesicles; cDNA—complementary DNA; Cry toxin—parasporal crystalline toxin of BT; IEF—immunoelectrophoresis; kb—kilobase or kilo base pairs; kD—kilodaltons; K$_d$—dissociation constant; LC$_{50}$—lethal concentration resulting in a 50% mortality; PBW—pink bollworm, *Pectinophora gossypiella* or *P. gossypiella;* PCR—polymerase chain reaction; RACE—Rapid Amplification of cDNA Ends; RT—reverse transcriptase; SW—silkworm (*Bombyx mori* or *B. mori*); THW—tobacco hornworm (*Manduca sexta* or *M. sexta*); and UTR—untranslated region.

The term "x % homology" refers to the extent to which two nucleic acid or protein sequences are identical as determined by BLAST homology alignment as described by T. A. Tatusova & T. L. Madden (1999), "Blast 2 sequences—a new tool for comparing protein and nucleotide sequences", FEMS MICROBIOL LETT. 174:247–250 and using the following parameters: Program (blastn) or (blastp) as appropriate; matrix (OBLOSUM62), reward for match (1); penalty for mismatch (−2); open gap (5) and extension gap (2) penalties; gap x-drop off (50); Expect (10); word size (11); filter (off). An example of a web based two sequence alignment program using these parameters is found at http://www.ncbi.nlm.nih.gov/gorf/bl2.html.

The invention thus includes nucleic acid or protein sequences that are highly similar to the sequences of the present invention, and include sequences of 80, 85, 90, 95 and 98% similarity to the sequences described herein.

The invention also includes nucleic acid sequences that can be isolated from genomic or cDNA libraries or prepared synthetically, and that hybridize under high stringency to the entire length of a 400 nucleotide probe derived from the nucleic acid sequences described herein under. High stringency is defined as including a final wash of 0.2×SSC at a temperature of 60° C. Under the calculation:

$$\textit{Eff Tm}=81.5+16.6(\log M\ [Na+])+0.41(\%\ G+C)-0.72(\%\ \text{formamide})$$

the percentage allowable mismatch of a gene with 50% GC under these conditions is estimated to be about 12%.

The nucleic acid and protein sequences described herein are listed for convenience as follows:

| SEQ ID Nos.: | DNA and Protein Sequences | |
|---|---|---|
| SEQ ID NO: 1 | BT-R2 cDNA sequence from *P. gossypiella* (FIG. 1) | |
| SEQ ID NO: 2 | BT-R2 protein sequence for *P. gossypiella* (FIG. 2) | |

| SEQ ID Nos.: | Primer Sequences | Primer Name |
|---|---|---|
| SEQ ID NO: 3 | 5' CAN ATH CGN GCN CAN GAY GGN GG 3' | BTR 1209U |
| SEQ ID NO: 4 | 5' TTG TAC ACS GCW GGS ATW TCC AC 3' | BTR 1355U |
| SEQ ID NO: 5 | 5' NAC YTG RTC RAT RTT RCA NGT CAT 3' | BTR 1486D |
| SEQ ID NO: 6 | 5' NCC DAT NAG RTC NGA RTC RTT NGA 3' | BTR 1657D |
| SEQ ID NO: 7 | 5' TAG GTT GTA TCC TCA GTA TGA GGA 3' | PBW-BTR GSP-1 |
| SEQ ID NO: 8 | '5' CCA GAG TGG AGT CCA CCG CCA TA 3' | PBW-BTR GSP-2 |
| SEQ ID NO: 9 | 5' CTG AGT AAG TGT TAT CTT GAA AG 3' | PBW-BTR GSP-3 |
| SEQ ID NO: 10 | 5' CAN ATH CGN GCN CAN GAY GGN GG 3' | BTR 1209U |
| SEQ ID NO: 11 | 5' GAT AGC GGC CCC AGG AAC CAA CAA ACA GG 3' | PBW-BTR GSP-4 |
| SEQ ID NO: 12 | 5' AGT GCG AGT GCT TTG AAT CTG TGA 3' | PBW-B' IR P2U |
| SEQ ID NO: 13 | 5' GTC TCT TCT CAC CGT CAC TGT CAC T 3' | PBW-BTR P5U |
| SEQ ID NO: 14 | 5' GCA TGC TGG CAG TAG GTT GTA TC 3' | PBW-BTR P6D |
| SEQ ID NO: 15 | 5' GGC CAC GCG TCG ACT ACT AC 3' | (AUAP) |
| SEQ ID NO: 16 | 5' GGC CAC GCG TCG ACT ACT ACT TTT TTT TTT TTT T 3' | (AP) |

N = A, C, T, or G;
H = A, T, or C;
B = T, C, or G;
D = A, T, or G;
V = A, C, or G;
R = A or G;
Y = C or T;
M = A or C;
K = T or G;
S = C or G;
W = A or T

More particularly, the studies described herein were targeted toward the identification, cloning and characterization of novel Cry toxin receptors. One embodiment was directed to characterization and isolation of the heretofore unidentified Cry toxin receptor of the pink bollworm, *P. gossypiella*, hereinafter referred to as "PBW".

In order to identify and isolate the Cry toxin receptor of the PBW, toxicity was determined for five different Cry proteins (Cry1Aa, Cry1Ab, Cry1Ac, Cry3A and Cry11A) against neonate PBW larvae. It was determined that the lepidopteran-specific toxins (Cry1Aa, Cry1Ab and Cry1Ac)

showed high toxicity toward PBW larvae with a $LC_{50}$ ranging from 25–45 $ng/cm^3$ of insect diet, while the coleopteran specific (Cry3A) or the dipteran specific (Cry11A) toxins did not exhibit any detectable toxicity up to 2000 $ng/cm^3$ (FIG. 3).

The binding of the three lepidopteran-specific Cry1A toxins (Cry1Aa, Cry1Ab and Cry1Ac) to the BBMV of *P. gossypiella* was characterized in detail. Ligand blot experiments showed that proteins of 120 kD bind only the Cry1Ac toxin whereas a 200 kD protein binds to Cry1Aa, Cry1Ab and Cry1Ac toxins. It is now known that the 120 kD protein is a heat shock protein, although its relation to the Cry toxin effect is not understood.

In the case of the 175 kD cadherin-like Cry1Aa binding protein from *Bombyx mori*, $^{125}$I-labeled Cry1Aa binding was eliminated by the presence of unlabeled Cry1Aa, but additional band(s) of approximately 110 kD, identified by $^{125}$I-Cry1Aa ligand blots, failed to demonstrate a detectable degree of competition. Thus, it was determined that *P. gossypiella*, like *M. sexta* and *B. mori*, contains both high-affinity and low-affinity binding proteins for at least one Cry1A toxin and that the 200 kDa protein from PBW is a common binding protein for the lepidopteran-specific Cry1A toxins.

The detailed mechanism of the Cry1A toxin interaction with the midgut BBMV of the pink bollworm was determined. The equilibrium dissociation constants ($K_d$) calculated from the homologous competition assays (FIGS. 3A and 3B) are 16.5, 12.4 and 12.8 nM and the concentrations of binding sites are 3.7, 3.6 and 8.6 pmol/mg, for Cry1Aa, Cry1Ab and Cry1Ac, respectively. The Hill Coefficients for the three Cry1A toxins are between 0.6 and 0.8 for BBMV binding proteins (FIG. 3A), indicating that there is negative cooperativity in the binding of these toxins to the binding site(s) in the BBMV. Binding of the Cry1A toxins to BBMV proteins was specific and saturable. The toxin amount required for saturation of 460 µg of BBMV proteins was in the following order: Cry1Ac>Cry1Aa>Cry1Ab.

Immunoprecipitation of BBMV proteins with anti-Cry1Ab antiserum and subsequent ligand blotting with $^{125}$I-Cry1Ab toxin also showed binding of the toxin to an approximately 200 kD protein. The 200 kD protein is a single protein as shown by 2D-gel analysis (data not shown). A comparison between the 210 kD binding protein from *M. sexta* with a pI ~4.3 and the 200 kD binding protein from *P. gossypiella* (pI ~4.1) revealed that both proteins have almost the same pI. It was determined that the 200 kD PBW protein had some cross-reactivity with polyclonal antisera against the *M. sexta* BT-$R_1$ 210 kD protein.

In order to clone the PBW BT-$R_2$ gene, fully degenerate primers were designed based on the conserved amino acid sequences between that of the two receptors, tobacco hornworm ("THW") BT-$R_1$ and silkworm ("SW") BT-R175. The primer locations were designed to include or exclude a sequence thought by the present inventors to encode a region in the extracellular domain critical to toxin binding, hereinafter "READ" signature sequence. Hereinafter this binding fragment of the DNA sequence will be referred to as the "signature" region.

Three clones were obtained, PBW-421 (aa 1367–1496), PBW-866 (aa 1210–1496) and PBW-1373 (aa 1210–1675), which have about 50% nucleotide and about 60% amino acid sequence similarity to both THW BT-$R_1$ and SW BT-R175. The 421 bp and 866 bp clones encode proteins of about 21 and 32 kD, respectively. Although both expressed proteins cross-reacted with THW BT-$R_1$ polyclonal antisera, the 32 kD protein, but not the 21 kD protein, was shown to bind Cry1Ab toxin specifically with high affinity. The estimated $K_d$ value is about 17 nM, which is similar to the $K_d$ value obtained for BBMV. Similarly, an internal fragment from the PBW-866 clone did not bind toxin, but did cross-react with BT-$R_1$ antibodies. This data demonstrates that recognition by anti-BT-$R_1$ antibodies is insufficient to define a functional toxin receptor.

In order to obtain a cDNA sequence encoding the full-length receptor, the 5' and 3' ends of the PBW BT-$R_2$ receptor were first obtained using 5' and 3' RACE reactions followed by cloning of the full-length receptor cDNA using gene specific primers from the 5' and 3' UTR. The full-length cDNA clone (SEQ ID NO: 1) has an open reading frame of 1729 amino acids (SEQ ID NO:2), with a deduced molecular weight of 194 kD and a calculated pI value of 4.1, which is similar to the value determined by 2-D gel analysis.

The protein consists of three domains: extracellular, transmembrane and cytoplasmic. The protein sequence contains two hydrophobic regions, one at the amino terminus, characteristic of a signal peptide and one near the COOH-terminus (amino acids 1575–1600) that probably forms a transmembrane domain. The extracellular domain contains 12 cadherin-like motifs, in addition to, a membrane proximal region that contains two leucine zipper motifs. Eleven consensus sites for N-linked glycosylation are present in the extracellular region, which may account for the difference in apparent molecular mass between the native protein and the calculated mass.

Based on the results discussed above, it would be apparent to one of ordinary skill in the art that variances in receptor sequences or in toxin binding affinities or in receptor expression may render different levels of toxin susceptibility or resistance. Furthermore, the receptor of the present invention may be used to generate transgenic organisms by methods well known in the art.

To investigate the mode of action of BT toxin, a mammalian heterologous cell culture system was chosen for several reasons. First, BT Cry1A toxins have shown no toxic effect on any mammalian cell lines studied to date. This characteristic is in contrast to most available insect cell lines, which exhibit variable degrees of sensitivity to toxin (Kwa et al., 1998). Second, the use of a mammalian cell would allow the determination of whether the receptor, independent of any associated protein in an insect cell line, would mediate toxicity.

When introduced into mammalian COS-7 cells, the cloned cDNA expressed BT-$R_2$ that was detected by western blot analysis using BT-$R_1$ antisera. The expressed receptor was displayed on the cell surface and detected with polyclonal antibodies raised against *M. sexta* BT-$R_1$. These results suggest that the protein expressed by the PBW BT-$R_2$ cDNA is similar to the natural protein found in the insect midgut.

The possibility of using COS-7 mammalian cells transfected with a receptor for BT toxins as a model system for assessing the cytotoxicity of the Cry1A toxin was determined. The surface receptor clearly was able to bind to the Cry1Ab toxin, which was detected by immunofluorescent labeling using Cry1Ab antibodies (data not shown). These results indicate that the binding site of the receptor must assume its native conformation. Significantly, intensively labeled vesicles in the methanol fixed transfected COS-7 cells were observed when the cells were incubated with BT-$R_1$ antiserum (data not shown). This observation indicates that vesicles, which form normally in the cell endocytosis/exocytosis pathway, contain the BT-$R_2$ proteins. In addition, this result shows that the receptor is not only expressed on the cell surface, like its native counter part in the insect midgut, but also is recycled normally by the cell.

Microscopy of the transfected COS-7 cells treated with Cry1Ab toxins for various times demonstrated significant cytopathological patterns. The cytopathological changes observed under the fluorescent microscope included disruption of the plasma membrane, cell swelling, disintegration and death of the cells. The symptoms were obtained in the presence of 0.6 µg/ml Cry1Ab for 2 hr. In contrast, no cytopathological effects were revealed for cells transfected with vector alone and subsequently treated with toxin. Clearly, there is a distinct correlation between toxin binding to the surface receptor and toxicity to the cells.

The cytological appearance and ultrastructure of the midgut cells of M. sexta and other lepidopteran larvae, after intoxication with preparations of BT, have been reported extensively by several authors (Bravo et al., 1992). Histopathological studies on M. sexta midgut demonstrated pathological behavior for Cry1A on midgut epithelial cells (columnar cells) (Midhoe et al., 1999). These investigators demonstrated that the epithelial cells of the midgut swell shortly after ingestion of the BT toxin. Eventually, the epithelial cells burst and released their cytoplasmic contents into the midgut lumen.

The present observations on the intoxicated transfected COS-7 cells are in complete agreement with these reports, which demonstrates that the toxin acts similarly in both systems. Furthermore, it should be apparent to one of ordinary skill in the art that cells expressing transfected molecules of the BT toxin receptor as well as cells expressing a natural form of the receptor may be used to asses the level of cytotoxicity and mode of action of toxins.

Lepidopteran insects generally express high molecular weight binding proteins for the Cry1A toxins that range in size from 160 to 220 kD (Martinez-Ramirez 1994; Vadlamudi et al.; 1993, Oddouet al., 1993; Nagamatsu et al., 1998a; Ihara et al., 1998). Two of these proteins, in addition to the 200 kD pink bollworm receptor, have been cloned and sequenced: the BT-$R_1$ 210 kD cadherin-related receptor from M. sexta (Vadlamudi et al., 1995) and the 175 kD cadherin-related from B. mori (Nagamatsu et al., 1998a). Interestingly, these two proteins have 60–70% identity and 80% similarity between themselves.

Figure 4:
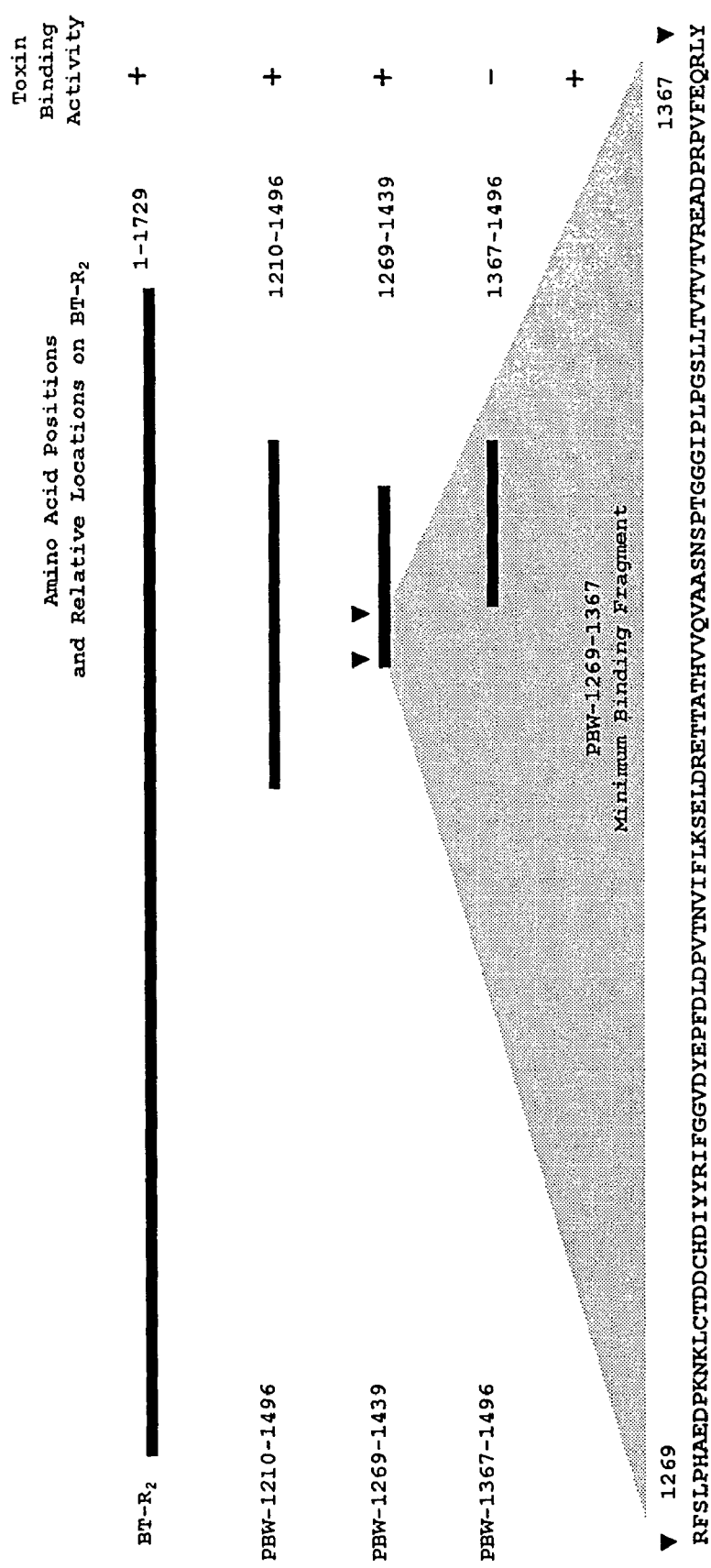
FIG. 4 is a map of the structure of the pink bollworm (PBW) BT-R$_2$ cDNAs, including truncations PBW-1210–1496, PBW-1269–1439, PBW-1367–1496, and PBW-1269–1367 of SEQ ID NO:2 (the minimum binding fragment). The binding of proteins expressed from each clone to Cry1A toxin was identified by (+) for binding and (−) for non-binding.

P. gossypiella expresses a high-affinity and a low-affinity binding protein for at least one Cry1A toxin, Cry1Ac. The high-affinity receptor is a cadherin-related protein with a large molecular mass. One of the most important conserved regions may be the signature sequence. The signature sequence contains the sequence (READ), which is believed to be responsible for toxin binding due to the presence of two negatively charged amino acids that bind to two arginines in the toxin binding site. Supporting evidence comes from the immunoblot analysis for clones PBW-866, which contains the proposed signature sequence, and PBW-421, which does not include the signature sequence. To further define the minimum binding fragment, truncation peptides were tested for their ability to bind toxin (FIG. 4). The minimum binding fragment contains the "READ" signature sequence and consists of amino acids 1269 to 1367.

The information provided herein is necessary for understanding the molecular biology of the toxin receptor in the pink bollworm and to engineer more effective toxins in terms of longer persistence in the field, higher toxicity, and preclusion of resistance development. This information will facilitate understanding of Cry toxin receptor interactions in other economically important insect crop pests.

EXAMPLE 1

Specificity of Purified Toxins

Recombinant protoxins Cry1Aa, Cry1Ab, and Cry1Ac (Bacillus Genetic Stock Center, Ohio State University) were prepared from E. coli JM-103 and trypsinized essentially as described by Lee et al. J. Biol. Chem. (1992) 267: 3115. In addition, the soluble trypsinized 60 kD toxins were subjected to FPLC NaCl salt gradient purification over an HR-5/5 Mono-Q anion exchange column (PHARMACIA™) prior to quantitation, radio-iodination, and use in bioassays. Cry3A crystal protein from B. thuringiensis subsp. tenebrionis was solubilized in 3.3 M NaBr and treated with papain, and the resulting 67 kD toxin was purified by the method of Li et al. Nature (1991) 353: 815. The 65 kD Cry11A toxin was isolated from B. thuringiensis subsp. israelensis via solubilization as described by Chilcott et al. J. Gen. Micro (1988) 134: 1551 and further purified by anion-exchange FPLC. All toxin protein quantitations were performed using the bicinchoninic acid method (PIERCE CHEMICAL™) with Bovine Serum Albumin (BSA, Fraction V) as a standard.

Pink bollworms were obtained from the USDA PINK BOLLWORM REARING FACILITY™ (PBWRF, Phoenix, Ariz.). An artificial diet was obtained from SOUTHLAND PRODUCTS INC.™, Lake Village, Ariz. The diet was reconstituted in boiling water and cooled to 55° C. Each Cry toxin was thoroughly mixed in the warm liquid diet and bioassay cups were filled with 20 ml of diet. After cooling and drying, 10 neonate larvae were placed in each cup and the cups were immediately capped. The method of Watson, et al., Beltwide Cotton Conference, Memphis, Tenn. (1995) was used to determine the toxicity of trypsin-activated toxins against first-instar larvae of P. gossypiella. Generally, four replicates of six cups were prepared for each dose. Cups were incubated at 30° C. for 21 days, the length of time necessary for more than 95% of normal P. gossypiella to reach pupation. At the end of 21 days, the diet cups were examined and the numbers of larvae and numbers of pupae or adults in each cup were recorded.

Figure 3B:
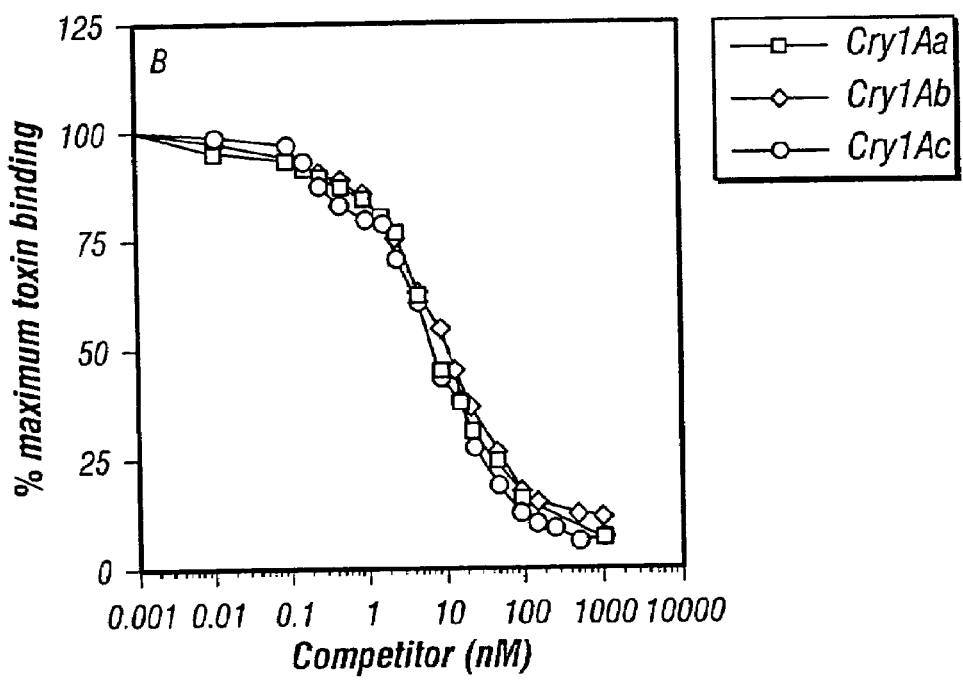
FIG. 3B is a graph showing the toxicity results of Cry1A toxins on *P. gossypiella* larvae and BBMV.

The specific toxicities of purified Cry1Aa, Cry1Ab, Cry1Ac, Cry3A and Cry 2A tested using neonate P. gossypiella larvae are shown in FIG. 3B. It was determined that all three Cry1A toxins are highly toxic, with $LC_{50}$ values ranging from 25–45 ng/cm$^3$ of artificial diet. Cry3A (considered toxic to coleopteran or beetle insects) and Cry IIA (considered toxic to dipteran insects, especially mosquitoes) were not toxic to P. gossypiella larvae at the highest concentrations tested (2000 ng/cm$^3$)

EXAMPLE 2

Characterization of the BT-$R_2$ Receptor

Early fourth-instar larvae were kept on ice for 1 hr and midguts were surgically removed from the larvae. BBMW were prepared from midgut tissues by the differential magnesium precipitation method of Wolfersberger, et al., Comp. Biochem. Physiol. (1987) 86A: 30, in the presence of protease inhibitors (5 mg/ml pepstatin, antipain, aprotonin, leupeptin, 1 mM PMSF, and 5 mM benzamidine). The final pellet was resuspended in buffer A (300 mM mannitol, 5 mM EGTA, and 17 mM Tris-HCl, pH 7.5) containing the protease inhibitors, flash frozen in liquid nitrogen, and stored at −85° C.

Cry toxins were radioiodinated using the chloramine T method (Hunter and Greenwood, *Nature* (1962) 194: 495, with $^{125}$I—Na (NEN DUPONT™). Ten μg of toxin were mixed with 5 μl of $^{125}$I—Na (0.5 mCi) in 100 μl of NaHPO$_4$ buffer (0.5 M, pH 7.4) with 25 μl of Chloramine T (4 mg/ml). The reaction mixture was agitated for 20–25 seconds at 23° C. and the reaction was stopped by adding 50 μl of Na$_2$S$_2$O$_5$ (4.4 mg/ml). Free iodine was removed by gel filtration on an EXCELLULOSE™ desalting column (PIERCE™) equilibrated with PBS containing 10 mg/ml BSA.

Toxin Binding Assays.

Both homologous and heterologous competition inhibition binding assays were performed as described by Keeton and Bulla (1997). A total of 25 μg of BBMV were incubated with 1.2 nM $^{125}$I-Cry1Ac toxin in the presence of increasing concentrations (0–1000 nM) of the appropriate unlabeled homologous toxin (Cry1Ac) or heterologous toxins (Cry1Aa, Cry1Ab, Cry3A, and Cry11A). Incubations were in 100 μl of binding buffer (PBS/0.2% BSA) at 25° C. for 30 min. Radiolabeled and unlabeled toxins were mixed together before adding them to the BBMV. Unbound toxins were separated from BBMV-bound toxin by centrifugation at 14,000×g for 10 min. The pellet containing bound toxin was washed three times in ice cold binding buffer by gentle vortexing and radioactivity in the final pellet was measured using a BECKMAN GAMMA 5500™ counter. Binding data were analyzed by the PRISM™ program (GRAPHPAD SOFTWARE INC.™, San Diego).

Competition inhibition binding of $^{125}$I-Cry1Ac toxin to *P. gossypiella* was carried out in the presence of increasing concentrations of unlabeled Cry1Ac, Cry1Ab, Cry1Aa, Cry3A and Cry11A toxins. Homologous competition binding assays were performed with iodinated Cry1A toxins and various concentrations of the corresponding unlabeled toxin. The binding site concentration ($B_{max}$), and dissociation constant ($K_d$) of labeled toxins were calculated from three separate experiments. The equilibrium binding parameters were estimated by analyzing the data with the PRISM™ computer program.

Radioligand Blotting.

The two hundred μg of BBMW proteins were solubilized, separated by 7.5% SDS-PAGE and transferred to polyvinylidene difluoride (PVDF) membrane as described by Francis and Bulla (1997). Blots were blocked with TBS (10 mM Tris-HCl and 0.9% NaCl) containing 5% non-fat dry milk powder, 5% glycerol 0.5% Tween-20, and 0.025% sodium azide for 2 hr at 25° C. Blocking buffer was removed and membranes were incubated for 2 hr at 25° C. in an equal volume of fresh blocking buffer containing 2×10$^5$ cpm/ml (1–1.25 nM) of $^{125}$I-Cry1A toxins either in the presence or absence of unlabeled toxins. Finally, membranes were washed three times with fresh blocking buffer for 10 min each, rinsed once with TBS, dried, and exposed to Kodak X-ray film at −80° C.

To determine the specificity of binding to the 200 and 120 kD proteins, blots of PBW BBMV proteins was incubated with $^{125}$I-Cry1Ac toxin in the presence of increasing concentrations of unlabeled Cry1Ac toxin.

Immunoprecipitation of Cry1Ab Binding Protein.

Immunoprecipitation was carried out according to Vadlamudi, et al. (1993). Twenty five μl of Cry 1Ab antiserum were added to 1 ml of protein A-Sepharose CL-4B equilibrated in washing buffer (1% Nonidet P-40, 6 mM EDTA, 50 mM Tris-HCl and 250 mM NaCl) and mixed for 1 hr at 4° C. After washing the blot three times with washing buffer, 700 μg of Cry 1Ab toxin were added and the mixture were incubated for an additional 1 hr at 4° C. and washed again three times with washing buffer. Pink bollworm BBMV proteins (6 mg) were solubilized in washing buffer containing 1% NP-40 and protease inhibitors (10 μg/ml pepstatin, antipain, aprotonin and leupeptin; 5 mM iodoacetamide; and 1 mM PMSF). Unsolubilized proteins were removed by centrifugation. Solubilized proteins were filtered through a 0.45 μm filter, added to 1 ml of Sepharose-protein A beads linked to Cry1Ab toxins, and the sample was stirred gently for 1 hr at 4° C. Sepharose beads were centrifuged and washed four times with washing buffer containing 0.25% NP-40 and 0.02% SDS. The toxin-binding protein complex was dissociated by heating in Laemmli (1970) sample buffer and the binding proteins were Coomassie stained and detected by ligand blotting with 125I-Cry1Ab and Western blot using Cry1Ab antiserum.

Immunodetection of Pink Bollworm Cry1A Receptor.

Immunoprecipitated proteins were transferred to a PVDF membrane, blocked with 5% nonfat dry milk in PBS buffer and incubated at 4° C. overnight in the same blocking buffer containing 10 μg/ml of Cry1Ab. Unbound toxin was washed with PBS. Antibodies raised in rabbits against the 60 kD Cry1Ab toxin were diluted 1:1000 and hybridized to the membrane for 2 hr at 25° C. and the blot then was washed with PBS. Peroxidase-conjugated goat anti-rabbit IgG was diluted 1:3000 in TBS blocking buffer and hybridized to the membrane for 2 hr. The membrane then was washed extensively with PBS. Visualization of the bound toxin was accomplished using the Enhanced Chemiluminescence (ECL) Western blotting detection method (AMERSHAM™).

Southern Blot Analysis.

Forty μg of PvuII digested genomic DNA from *P. gossypiella* or *M. sexta* were separated on a 0.8% 1× TBE-agarose gel and blotted onto a nylon membrane (BIO-RAD™, ZETA-PROBE GT™). The analysis was carried out according to Sambrook, et al. *Molecular Cloning: A Laboratory Manual*, 2$^{nd}$ Ed. Cold Spring Harbor Laboratory, N.Y. (1989). The filter was hybridized with $^{32}$P-labeled, random primed, C-terminal of BT-R$_1$ cDNA (HincII fragment, 0.5 kb). Filter hybridization was carried out at 42° C. for 21 hr in 50% formamide, 5× Denhardt's reagent, 1M NaCl, 2% SDS, 50 mM Tris-HCl and 100 μg/ml of salmon sperm DNA. The filter was washed with 2×SSC, 0.5% SDS, then with 1×SSC, 0.5% SDS, then with 0.5×SSC, 0.5% SDS, followed by a fourth wash with 0.25×SSC, 0.5% SDS. Each wash was for 30 min at 42° C. Finally, the filter was rinsed in 2×SSC and exposed to Kodak X-ray film at −85° C.

Electrophoretic Elution of Proteins.

Electrophoresis was performed in 1.5-mm-thick polyacrylamide slab gels using 7.5% acrylamide (pH 8.0). After SDS-PAGE, proteins were revealed as transparent bands with 4 M sodium acetate solution. The proteins were excised using a razor blade. Proteins in the gel strips were fixed in 50% (v/v) methanol solution for 15 min and equilibrated twice in 0.125 M Tris-HCl buffer (pH 6.8) and 2% 2-mercaptoethanol for an additional 15 min. Equilibration of the gel strips in the above buffer with 1% (w/v) SDS was performed as described above. The equilibrated gel strips were inserted into a dialysis tube with a minimum amount of the buffer containing SDS (25 mM Tris, 190 mM glycine and 0.1% SDS). Electroelution was carried out essentially as described by Findlay (1990). A horizontal flat-bed mini-gel electrophoresis apparatus (BIO-RAD™) was used for electroelution at 50 V for 12 hr at 4° C. The buffer consisted of 25 mm Tris, 190 mM glycine and 0.1% SDS (pH 8.3). At the end of electrophoresis, the polarity of electrodes was changed for 30 sec to avoid adsorption of proteins onto the dialysis tubes. The buffer inside the dialysis tubes was collected and the tubes were washed three times with a minimum volume of buffer. SDS was dialyzed out and protein was concentrated by using a CENTRICON-30 micro-concentrator (AMICON).

Two-Dimensional Gel Electrophoresis.

Two-dimensional gel electrophoresis was performed according to the method of O'Farrell (1975). Isoelectric focusing was carried out in 2.0 mm (I.D.) glass tubes using 2.0% ampholines (pH 3.5–10; LKB/PHARMACIA™) for 9600 volt-hr. After equilibration for 10 min in buffer 'O', tube gels were applied to the stacking gels on top of 8% acrylamide (pH 8.0) slab gels (14×14 cm). SDS slab gel electrophoresis was carried out for 4 hr at 12.5 mA. After electrophoresis, one gel was stained with Coomassie blue and the others were transblotted onto PVDF paper overnight at 200 mA (Vadlamudi et al., 1993). The PVDF paper was blocked with powdered milk solution, incubated with $^{125}$I-Cry1Ac or $^{125}$I-Cry1Ab and exposed to X-ray film at −85° C.

Identification and Recovery of cDNA Encoding BT-$R_2$.

Total RNA was prepared from the midgut tissue of fourth instar larvae of the PBW by the guanidinium thiocyanate method (Chomczynki et al. *Analyt. Biochem.* (1987) 162: 156). Poly (A+) RNA was isolated with the POLYATRACT MRNA ISOLATION SYSTEM™ (PROMEGA™). First strand cDNA was synthesized using oligo-(dT) and random hexamer primers and reverse transcriptase according to standard methodologies and used as the template for amplification by polymerase chain reaction (PCR) of desired mRNAs. Degenerate oligonucleotide primers were designed based on the conserved amnio acids between *M. sexta* BT-$R_1$ and *B. mori* BT-R175. Such primers were used to clone partial fragments of PBW BT-$R_2$.

For cloning of the PBW BT-$R_2$, RT-PCR was employed using fully degenerate oligonucleotide primers derived from a sequence in the membrane proximal domain conserved sequence between *M sexta* BT-$R_1$ and *B. mori* BT-R175. Primers BT-R-1355U and BT-R-1209U against BT-R-1486D were applied to PBW cDNA to amplify 421-bp and 866-bp fragments. The PCR products were resolved on 1.5% agarose, gel purified, cloned into a TA cloning vector (INVITROGEN™) and transformed into *E. coli* INV∝F. The presence and identity of the correct insert was confirmed with EcoR1 digestion and DNA sequencing. The PBW-886 clone was found to contain the nucleotide sequence found in clone PBW-421. In addition, primer 1209U against 1657D was used to clone a 1373-bp fragment (PBW-1373), which represents most of the membrane proximal domain and the cytoplasmic domain. Clone PBW-287 (aa 1346–1438) is a 287 bp internal fragment from 866-bp clone and was cloned using gene specific primers P5 and P6.

Based on the sequence obtained from the partial clones, sense and antisense primers were used to clone the 3' and 5' ends of the PBW BT-$R_2$ clone by the 5' and 3' RACE system according to the manufacturer's instructions (GIBCO BRL™). The 5' end was amplified using gene-specific antisense primers GSP1, GSP2 and GSP3 against ABRIDGED UNIVERSAL AMPLIFICATION PRIMER™ (AUAP™) provided in the kit. The 3' end was amplified using gene primer GSP4 against AUAP™. The PCR product of the predicted size was isolated and subcloned into TA cloning vector pCR2.1 (INVITROGEN™) and transferred into *E. coli* INV∝F. For recombinant protein expression in *E. coli*, or COS7 cells, the coding sequences for the RT-PCR clones or the full length PBW-BT-$R_2$ clone were recloned into the pET30 or pcDNA3.1 expression vectors and transformed into BL21 (DE3) LysS (NOVAGEN™) or COS7 mammalian cells. The *E. coli* cultures were induced using a 1 mM final concentration of IPTG for 3 hr.

The full length PBW BT-$R_2$ (~5.5 kb; see sequence in FIG. 1 SEQ ID NO:1) was ligated into the mammalian expression vector pcDNA3.1 (INVITROGEN™) and confirmed by DNA sequencing. The molecular mass of the deduced polypeptide is 194 kD with a pI of 4.1. The receptor has an open reading frame of 1729 amino acids (FIG. 2) (SEQ ID NO: 2). The amino acid sequence contains a putative signal peptide of 23 amino acid residues, a transmembrane domain of 27 residues (aa 1578–1605) and a 124-residue cytoplasmic domain. In addition, the amino acid sequence contains 12 putative cadherin motifs, 11 putative N-glycosylation sites and two leucin zipper motifs at amino acid 1541–1562 and 1578–1600. The minimum toxin binding fragment is amino acids 1269 to 1367 (FIG. 4).

When the protein homology is analyzed by BLASTP, as described under definitions above, the closest paralog in the GenBank nonredundant (nr) database is the *Bombyx mori* receptor at Acc. No. JE0128 with Identities=1034/1708 (60%), Positives=1266/1708 (73%), Gaps=35/1708 (2%). The next closest species was *Manduca sexta* at Acc. No. AAB33758.1 with Identities=871/1540 (56%), Positives=1101/1540 (70%), Gaps=22/1540 (1%). The nucleotide sequence showed no significant homologies.

The peptide homologies amongst these three species are shown in FIGS. 5A–C where perfectly conserved residues are boxed. Peptide fragments of the SBW sequence may be used to generate specific or nonspecific antibodies. Usually, it is recommended that at least 17 amino acid peptide fragments are used to generate antibodies, however, smaller peptides may also be antigenic and sufficiently complex to be unique. In particular, the carboxyl tail (aa 1677-end) of the PBW sequence is unique to this species and can be used to generate PBW unique antibodies. Exemplary peptides that may be useful as antigens (numbered with respect to FIG. 5, SEQ ID NO: 2) are shown as follows:

| PBW Unique Peptides | Common Peptides |
|---|---|
| aa 534–544 | aa 291–304 |
| aa 697–705 | aa 622–632 |
| aa 886–895 | aa 791–803 |
| aa 1055–1066 | aa 1621–1642 |
| aa 1321–1331 | |
| aa 1451–1461 | |
| aa 1516–1525 | |
| aa 1572–1582 | |
| aa 1677–1729 | |

Immunodetection of the Expressed BT-$R_2$ Proteins.

Cell lysates from the induced BL21 (DE3) LysS bacterial cultures were electrophoresed and transferred to PVDF membranes. Filters were blocked at 4° C. in 50 ml of blocking buffer containing 10 ug/ml of Cry1Ab toxin. Unbound toxin was removed by PBS. Rabbit primary antibodies for the THW was removed by PBS. Rabbit primary antibodies for the THW BT-R, extracellular domain or for the FPLC-purified Cry1Ab were diluted 1:1000 in 50 ml TBS blocking buffer. The filters were incubated for 2 hr with the antiserum and washed three times with the blocking buffer. Peroxidase-conjugated goat anti-rabbit IgG was diluted to 1:2000 and incubated with filters for 2 hr at 27° C. and was developed with the enhanced chemoluminescence (ECL) detection system (AMERSHAM™).

Mammalian Expression of BT-$R_2$.

The PBW BT-$R_2$ cDNA cloned into pcDNA3.1, a mammalian expression vector (INVITROGEN™), was expressed in mammalian cells (COS-7 SV40 transformed African green monkey cells; ATCC CRL-1651) according to methods described by Keeton and Bulla, *Appl. Environ. Microbiol.* (1997) 63: 3419. COS-7 cells ($4 \times 10^4$/well) were grown in Dulbecco's Modified Eagle Medium (DMEM) supplemented with 10% heat-inactivated fetal bovine serum (FBS) on 12 mm cover slips placed in a 24-well plate.

COS-7 cells were transfected with the construct using the LIPOFECTAMIN PLUS REAGENT™ (GIBCO BRL™). The cells were incubated for two days at 37° C. in DMEM medium containing 10% FBS in a humidified atmosphere of 10% $CO_2$. BT-$R_2$ was monitored by SDS-PAGE and immunoblotting with anti-BT-$R_1$ or antiCry1Ab antiserum. Surface expression was detected by immunofluorescence microscopy with the anti-BT-$R_1$ antibodies. The effects of BT toxin on the transfected cells were demonstrated by incubating the cells in the presence or absence of Cry1Ab toxin for 2 or 4 hr and monitoring the morphological changes by immunofluorescence microscopy using either anti-BT-$R_1$ or anti-Cry1Ab antibodies. Cell death is clearly demonstrated (not shown).

Immunoflourescene Microscopy.

COS-7 cells were grown on 12-mm glass coverslips in a 24-well plate. The cells were fixed and permeabilized either in cold methanol (−20° C.) or 4% paraformaldhyde for 15 minutes at 27° C. Coverslips were rinsed three times with PBS and then blocked for 15 minutes with 1% BSA in PBS. Cells were incubated with primary antibody for 30 minutes at 27° C. followed by rinsing and blocking as just described. The same incubation and washing procedures were applied to secondary antibody. Antibodies were detected with TRITC goat anti-rabbit IgG. Coverslips were mounted in FLUROMOUNT G™ and viewed with an OLYMPUS™ microscope equipped with epi-fluorescence illumination and a 40× Apochromat lens. Photography was done with an OLYMPUS SPOT™ camera.

Western Blot Analysis.

Transfected COS-7 cells were washed with cold PBS, lysed in lysis buffer (50 mM Tris/HCL, 1 mM EDTA, 10 µM leupeptin) and resuspended on ice for 10 minutes. Then, 4× sample buffer was added to the cells and heated at 95° C. for 5 minutes. Lysates were subjected to electrophoresis through 7.5% SDS-PAGE, and proteins were electrophoretically transferred to a PVDF filter, blocked and incubated with either anti-BT-$R_1$, or anti-Cry1Ab antibodies.

Results: Identification of $^{125}$I-Cry1A Binding Proteins.

BBMV proteins of *P. gossypiella* ranged in molecular size from greater than 205 kD to less than 25 kD (data not shown) as determined by SDS-PAGE. $^{125}$I-labeled Cry1Aa, Cry1Ab and Cry1Ac were used in ligand blots to identify which *P. gossypiella* BBMV proteins bind the respective toxins. Proteins that had been separated by SDS-PAGE were transferred to PVDF membranes and incubated with each radiolabeled-toxin separately. $^{125}$I-Cry1Aa, $^{125}$I-Cry1Ab and $^{125}$I-Cry1Ac bound to a protein of about 200 kD (data not shown). $^{125}$I-Cry1Ac bound also to a protein band at about 120 kD. Neither Cry1Aa nor Cry1Ab bound to the 120 kD protein. The binding patterns for all three toxins were the same under both reducing and nonreducing conditions (data not shown).

Results: Competition Inhibition Binding Assays.

$^{125}$I-labeled Cry1Aa, Cry1 Ab and Cry1Ac were used in binding assays with *P. gossypiella* BBMV. Competition binding of $^{125}$I-Cry1Ac toxin to *P. gossypiella* was carried out in the presence of increasing concentrations of unlabeled Cry1Aa, Cry1Ab, Cry1Ac, Cry3A and Cry11A toxins. Fifty-percent inhibition of Cry1Ac binding was observed at 10 nM of unlabeled Cry1Ac, 100 nM unlabeled Cry1Aa and 100 nM of unlabeled Cry1Ab. At a concentration of 1000 nm, unlabeled Cry1Ac, Cry1Ab and Cry1Aa reduced binding of iodinated Cry1Ac by 95, 82 and 80%, respectively (data not shown). Neither Cry3A nor Cry11A toxin competed for the Cry1Ac toxin binding site.

Homologous competition binding assays were performed with iodinated Cry1A toxins and various concentrations of the corresponding unlabeled toxin Cry1Aa, Cry1Ab and Cry1Ac showed high binding affinity to BBW proteins (data not shown). Fifty-percent inhibition of binding of Cry1A toxins was observed at concentrations of approximately 10 nM of the corresponding unlabeled toxin. These data indicate that each of the three toxins binds specifically with high affinity. The binding site concentration, $B_{max}$, and the dissociation constant, $K_d$, of each toxin was calculated from the three separate homologous competition inhibition experiments by analyzing the data with the GRAPHAD computer program (Table 1). The $K_d$ values all were similar and in the low nM range whereas the $B_{max}$ for Cry1Ac was higher than Cry1Aa or Cry1Ab. The Hill coefficients for Cry1Aa, Cry1Ab and Cry1Ac were 0.65, 0.65, and 0.77, respectively, indicating a negative binding cooperativity for the toxins against the BBMV proteins. A single binding site model was indicated based on the nonlinear regression analysis for both Cry1Aa and Cry1Ab. Significantly, Cry1Ac, the data was best accommodated by a two binding site model with high- and low-affinity binding sites.

Results: Specificity of $^{125}$I-Cry1Ac Toxin Binding in Ligand Blots.

In view of the putative "two-binding site" model predicted for the Cry1Ac toxin, radioligand blots of *P. gossypiella* BBMV proteins were carried out with $^{125}$I-Cry1Ac toxin in the presence of increasing concentrations of unlabeled Cry1Ac toxin. Autoradiography of these blots revealed significant reduction in the intensity of the 200 kD band (data not shown). Indeed, it was undetectable at a Cry1Ac toxin concentration of 10 nM. In the case of the 120 kD band, however, there was virtually no reduction in the band intensity (data not shown) even at a Cry1Ac concentration of 1000 nM. In saturation binding assays, incubation of a fixed amount of each of the three $^{125}$I-labeled Cry1A toxins with increasing concentrations of BBMV showed that binding reached a saturation level in each case but that the level of Cry1Ac binding was substantially higher than those of Cry1Aa and Cry1Ab. Maximum saturable binding at 400 µg/ml of BBMV was approximately 0.35, 0.05 and 1.5 ng for Cry1Aa, Cry1Ab and Cry1Ac, respectively, which represents an approximately 30-fold difference in Cry1Ac binding compared to Cry1Ab, and, it is 4 fold higher for Cry1Ac compared to Cry1Aa (data not shown).

Results: Immunoprecipitation of the Cry1Ab Binding Protein.

Immunoprecipitation experiments were performed using Cry1Ab, which has the highest binding affinity of the three toxins, to further examine the specificity of binding of the toxin to the 200 kD protein. BBMV proteins were solubilized in 1% NONIDET P-40™ and immunoprecipitated with anti-toxin-protein A-Sepharose beads. The mixture of bound material was solubilized in SDS sample buffer containing 2-mercaptoethanol. Electrophoresis and staining of the gel with Coomassie blue revealed a protein of about 200 kDa, demonstrating selective precipitation of the 200 kD toxin-binding protein. Radioligand blotting with $^{125}$I-Cry1Ab showed a band of about 200 kDa (data not shown), indicating precipitation of the same binding protein as that identified in previous ligand blot experiments. Additionally, a Western blot (data not shown) of the immunoprecipitated protein using Cry1Ab and anti-Cry1Ab polyclonal antiserum confirmed the results of the radio-ligand blot (data not shown). The low-molecular weight bands at 60 and 52 kDa correspond to the Cry1Ab toxin and the heavy chain of IgG, respectively.

Results: Purification of the Binding Proteins.

To determine whether the 200 kD band contains more than one protein, the band was excised from a 7.5% SDS polyacrylamide gel, electroeluted, dialyzed and concentrated. The concentrated protein was analyzed by two-dimensional gel electrophoresis over a pH range of 3.5–10. The protein migrated as one spot with an estimated pI of 4.5±0.2 and apparent molecular mass of 200 kDa. The purified 200 kD protein stained with Schiff's reagent (data not shown) indicating that the binding protein is glycosylated. The 200 kD IEF spot bound $^{125}$I-Cry1Ab (data not shown) corroborates the results from other immunoprecipitation studies.

Results: Southern Blot Analysis.

To detect the presence of the Cry1A receptor in *P. gossypiella*, genomic DNA from both insects were hybridized against the cloned THW BT-R$_1$ cDNA and its 507-bp minimum binding fragment. The two probes bound intensively to the PvuII fragment of *M. sexta* genomic DNA (data not shown). There was weak hybridization to the *P. gossypiella* DNA, however, using the minimum binding probe and none with the full-length BT-R$_1$ probe (data not shown). These results suggest that the minimum binding fragment from *M. sexta* shares a significant level of nucleotide similarity to the Cry1A binding receptor in *P. gossypiella*, more so than to the full-length BT-R$_1$ receptor.

Results: Immunodetection of Native and Cloned PBW BT-R$_2$ Using BT-R$_1$ Antibodies.

To confirm the relatedness of the cloned PBW fragment to the THW BT-R$_1$ and its ability to bind toxin, it was subcloned into a pET30 expression vector. The native PBW BBMV proteins and the expressed proteins from clones PBW-287, -421 and -866 were resolved by SDS-PAGE, transferred to a PVDF membrane and incubated with either anti-BT-R$_1$ serum or Cry1Ab toxin followed by antiserum to the toxin. The results reveal that BBMV contain a 200 kD protein that interacts with THW BT-R$_1$ antiserum (data not shown). In addition, clones PBW-287, -421 and -866 which express proteins of about 15, 21 and 32 kD, respectively, also cross-reacted with BT-R$_1$ antiserum. The 32 kD clone, however, was the only protein to bind toxin, whereas no detectable binding was observed with the 21 kD protein (data not shown). These results confirm the sequence relatedness of PBW BT-R$_2$ to THW BT-R$_1$ and demonstrate that the 32 kD protein contains the toxin-binding site of the receptor.

Results: Specificity of Toxin Binding to the Cloned Receptor.

The specificity and affinity of toxin binding to the receptor fragment (PBW-866) was determined using competition ligand blot analysis. The expressed 32 kD protein was transferred to PVDF membranes and incubated with $^{125}$I-Cry1Ab in the absence or presence of increasing concentrations of unlabeled Cry1Ab toxin. Autoradiography revealed significant reduction in the intensity of the 32 kD band to an undetectable level in the presence of 500 nM unlabeled Cry1Ab toxin (data not shown). Bound $^{125}$I toxin was quantitated with a gamma counter and the BIO-RAD IMAGER™ analysis system was used to calculate the binding affinity of toxin to the expressed fragment. The binding affinity (~17 nM) of the toxin was similar to the calculated value (Table 1) for BBMV. These results demonstrate that Cry1Ab binds specifically with high affinity to PBW BT-R$_2$ 866. Other truncation fragments were also tested, and it was determined that the minimum binding fragment consists of amino acids 1269 to 1367.

Results: Expression of PBW BT-R$_2$ in COS-7 Cells.

PBW BT-R$_2$ cDNA was subcloned into the mammalian expression vector pcDNA3.1 (INVITROGEN™) and transfected into COS-7 cells. Protein encoded by the PBW BT-R$_2$ cDNA was expressed as a membrane protein capable of binding Cry1Ab toxin. Membranes isolated from transiently transfected COS-7 cells were solubilized, electrophoresed, and immunoblotted either with Cry1Ab toxin and its antiserum or with BT-R$_1$ antiserum directly. The expressed 220 kD receptor bound Cry1Ab toxin and cross-reacted with BT-R$_1$ antiserum. No interaction to vector transfected cells was observed.

Expression of BT-R$_2$ receptor on the cell surface was shown by fixing the cells in methanol or paraformaldehyde and incubating first with anti-BT-R$_1$ serum, and then with TRITC IgG secondary antibodies. Transfected cells portrayed bright surfaces due to the binding of BT-R$_1$ antibodies to the cell surface clearly showing that the PBW BT-R$_2$ receptor is expressed on the cell surface.

The surface-expressed PBW receptor binds toxin and kills the cells. Transfected cells were incubated with Cry1Ab toxin for 2 or 4 hr, washed, fixed and incubated first with anti-Cry1Ab antiserum, and then with TRITC IgG secondary antibodies. As shown by immunofluorescence microscopy, BT-R$_2$ expressing COS-7 cells bound the toxin, whereas cells transfected with vector alone did not show any surface binding of toxin. Incubation of cells expressing PBW BT-R$_2$ with toxin for 2 or 4 hr showed significant morphological changes which include loss of cell integrity, loss of cell cytoplasm and complete disintegration of the plasma membrane and cell death.

The prior cited and following references are incorporated by reference herein and are used to support the invention disclosure:

J. S. Alexander et al., The role of cadherin endocytosis in endothelial barrier regulation: involvement of protein kinase C and actin-cadherin interactions, *Inflammation*, Vol. 22, pp. 419–433, 1998.

A. C. Bartlett, Resistance of the pink bollworm to B. T. transgenic cotton, *Beltwide Cotton Conf.*, Vol. 2, pp. 766–768, 1995.

P. C. Bolin et al., presented at the XXVIIth Annual Meeting of the society for Invertebrate Pathology, Cornell University, Ithaca, N.Y., 1995.

A. Bravo, Phylogenetic relationships of *Bacillus thuringiensis* delta-endotoxin family proteins and their functional domains, *J. Bacteriol*,. Vol. 179, pp. 2793–2801, 1997.

A. Bravo et al., Immunocytochemical Localization of *Bacillus thuringiensis* insecticidal crystal proteins in intoxicated insects, *J. Invertebr. Pathol*,. Vol. 60, pp. 237–246, 1992.

L. A. Bulla et al., Ultrastructure, physiology, and biochemistry of *Bacillus thuringiensis, Crit. Rev. Microbiol*,. Vol. 8, pp. 147–204, 1980.

J. Carroll et al., Analysis of the large aqueous pores produced by a *Bacillus thuringiensis* protein insecticide in *Manduca sexta* midgut-brush-border-membrane vesicles, *Eur. J. Biochem*,. Vol. 245, pp. 797–804, 1997.

N. C. Chilcott et al., Comparative toxicity of *Bacillus thuringiensis var. israelensis* crystal proteins in vivo and in vitro; *J. Gen. Micro*,. Vol. 134, pp. 2551–2558, 1988.

P. Chomczynki et al., Single-step method of RNA isolation by acid guanidinium thiocyanate-phenol-chloroform extraction, *Analyt. Biochem*,. Vol. 162, pp. 156–159, 1987.

A. H. Dantzig et al., Association of intestinal peptide transport with a protein related to the cadherin superfamily, *Science*, Vol. 264, pp. 430–433, 1994.

M. L. Day et al., E-cadherin mediates aggregation-dependent survival of prostate and mammary epithelial cells through the retinoblastoma cell cycle control pathway, *J. Biol. Chem.*, Vol. 274, pp. 9656–9664, 1999.

R. A. De Maagd, Different Domains of *Bacillus thuringiensis* δ-endotoxins can bind to insect midgut membrane proteins on ligand blots, *Appl. Environ. Microbiol*,. Vol. 62, pp. 2753–2757, 1996.

J. A. Dorsch et al., Isolation of the binding site in $BT-R_1$ from *Manduca sexta* for the insecticidal toxin of *Bacillus thuringiensis* subsp. *berliner*. In Preparation, 1999.

U. Estada et al., Binding of insecticidal crystal proteins of *Bacillus thuringiensis* to the midgut brush border of the cabbage looper, *Trichoplusia ni* (Hubner) (Lepidopteran: Noctuidae), and selection for resistance to one of the crystal proteins, *Appl. Environ. Microbiol*,. Vol. 60, pp. 3840–3846, 1994.

J. Ferre et al., Biochemistry and genetics of insect resistance to *Bacillus thuringiensis* insecticidal crystal proteins, FEMS Microbiol. Lett., Vol. 132, pp. 1–7, 1995.

J. B. Findlay et al., Gel Electrophoresis of proteins-A Practical Approach, *Academic Pree, New York*, $2^{nd}$ ed., B. D. Hames and D. Rickwood (editors), pp. 83–89, 1990.

B. B. Finlay et al., Exploitation of mammalian host cell functions by bacterial pathogens, *Science*, vol. 276, pp. 718–725, 1997.

B. R. Francis et al., Further characterization of $BT-R_1$, the cadherin-like receptor for Cry1Ab toxin in tobacco hornworm (*Manduca sexta*) midguts, *Insect Biochem. Mol. Biol*,. Vol. 27, pp. 541–550, 1997.

S. F. Garczynski et al., Identification of putative insect brush border membrane-binding molecules specific to *Bacillus thuringiensis* δ-endotoxin by protein blot analysis, *Appl. Environ. Microbiol*,. Vol. 57, pp. 2816–2820, 1991.

S. S. Gill et al., Identification, isolation, and cloning of a *Bacillus thuringiensis* Cry1Ac toxin-binding protein from the midgut of the lepidopteran insect *Heliothis virescens*, *J. Biol. Chem*,. Vol. 270, pp. 27277–27282, 1995.

S. S. Gill et al., The mode of action of *Bacillus thuringiensis* endotoxins, *Annu. Rev. Entomol*,. Vol. 37, pp615–636, 1992.

R. Gurezka et al., A heptad motif of leucine residues found in membrane proteins can drive self-assembly of artificial transmembrane segments, *J. Biol. Chem*,. Vol. 274, pp. 9265–9270, 1999.

J. L. Hermiston et al., In vivo analysis of cadherin function in the mouse intestinal epithelium: essential roles in adhesion, maintenance of differentiation, and regulation of programmed cell death, *J. Cell Biol*,. Vol. 129, pp. 489–506, 1995.

C. Hofmann et al., Binding of the delta endotoxin from *Bacillus thuringiensis* to brush-border membrane vesicles of the cabbage butterfly (*Pieris brassicae*), *Eur. J. Biochem.*, Vol. 173, pp. 85–91, 1998a.

C. Hofmann et al., Specificity of *Bacillus thuringiensis* delta-endotoxins is correlated with the presence of high-affinity binding sites in the brush border membrane of target insect midguts, *Proc. Natl. Acad. Sci. USA*, Vol. 85, pp. 7844–7848, 1988b.

H. Hofte et al., Insecticidal crystal proteins of *Bacillus thuringiensis, Microbiol. Rev*,. Vol. 53, pp. 242–255, 1989.

W. Hunter et al., Preparation of iodine-131 labeled human growth hormone of high specific activity, *Nature*, Vol. 194, pp. 495–496, 1962.

H. Ihara et al., Purification and partial amino acid sequences of the binding protein from *Bombyx mori* for Cry1Aa delta-endotoxin of *Bacillus thuringiensis, Comp. Biochem. Physiol. B. Biochem. Mol. Biol*,. Vol. 120, pp. 197–204, 1998.

S. S. Kantak et al., E-cadherin regulates anchorage-independent growth and survival in oral squamous cell carcinoma cells, *J. Biol. Chem*,. Vol. 273, pp. 16953–16961, 1998.

T. P. Keeton et al., Ligand specificity and affinity of $BT-R_1$, the *Bacillus thuringiensis* Cry1A toxin receptor from *Manduca sexta*, expressed in mammalian and insect cell cultures, *Appl. Environ. Microbiol*,. Vol. 63, pp. 3419–3425, 1997.

T. P. Keeton et al., Effects of midgut-protein-preparative and ligand binding procedures on the toxin binding characteristics of $BT-R_1$, a common high-affinity receptor in *Manduca sexta* for Cry1A *Bacillus thuringiensis* toxins, *Appl. Environ. Microbiol*,. Vol 64, pp. 2158–2165, 1998.

C. Kintner, Regulation of embryonic cell adhesion by the cadherin cytoplasmic domain, *Cell*, Vol. 69, pp. 225–236, 1992.

P. J. Knight et al., The receptor for *Bacillus thuringiensis* Cry1A(c) delta-endotoxin in the brush border membrane of the lepidopteran *Manduca sexta* is aminopeptidase N. *Mol. Microbiol*,. Vol. 11, pp. 429–436, 1994.

B. H. Knowles, Mechanism of action of *Bacillus thuringiensis* insecticidal δ-endotoxins, *Adv. Insect Physiol*,. Vol. 24, pp. 275–308, 1994.

K. A. Knudsen et al., A role for cadherins in cellular signaling and differentiation, *J. Cell Biochem. Suppl*,. Vol. 30-31, pp. 168–176, 1998.

J. S. Kwa et al., Toxicity and binding properties of the *Bacillus thuringiensis* delta-endotoxin Cry1C to cultured insect cells, *J. Invertebr. Pathol*,. Vol. 71, pp. 121–127, 1998.

U. K. Laemmli, Cleavage of structural proteins during the assembly of the head of bacteriophage T4, *Nature*, Vol. 227, pp. 680–685, 1970.

M. K. Lee et al., Inconsistencies in determining *Bacillus thuringiensis* toxin binding sites relationship by comparing competition assays with ligand blotting, *Biochem. Biophys. Res. Commun,*. Vol. 220, pp. 575–580, 1996.

M. K. Lee et al., Location of *Bombyx mori* receptor binding region of a *Bacillus thuringiensis* δ-endotoxin, *J. Biol. Chem,*. Vol. 267, pp. 3115–3121, 1992.

M. K. Lee et al., Resistance to *Bacillus thuringiensis* CryIA delta-endotoxins in a laboratory-selected Heliothis virescens strain is related to receptor alteration, *Appl. Environ. Microbiol,*. Vol. 61, pp. 3836–3842. 1995.

J. Li et al., Crystal structure of the insecticidal δ-endotoxin from *Bacillus thuringiensis* at 2.5 Å resolution, *Nature*, Vol. 353, pp. 815–821, 1991.

K. Luo et al., A 106 kDa from of aminopeptidase is a receptor for *Bacillus thuringiensis* Cry1C d-endotoxin in the brush border membrane of *Manduca sexta, Insect Biochem. Mole., Biol,*. Vol. 26, pp. 783–791, 1996.

K. Luo et al., Binding of *Bacillus thuringiensis* Cry1Ac toxin to aminopeptidase in susceptible and resistant Diamondback moths (*Plutella xylostella*), *Appl. Environ. Microbiol,*. Vol. 63, pp. 1024–1027, 1997.

A. C. Martinez-Ramirez et al., Ligand blot identification of a *Manduca sexta* midgut binding protein specific to three *Bacillus thuringiensis* Cry1A-type ICPs, *Biochem. Biophys Res. Commun,*. Vol. 201, No. 2, pp. 782–787, 1994.

J. Mengaud et al., E-cadherin is the receptor required for internalin, a surface protein required for entry of *L. monocytogenes* into epithelial cells, *Cell*, Vol. 84; pp. 923–932, 1996.

E. G. Midboe, Characterization of the BT-R$_1$ gene and its expression in *Manduca sexta*, Ph.D. University of Wyoming, Laramie.

W. J. Moar et al., Development of *Bacillus thuringiensis* Cry1C resistance by *Spodoptera exigua* (Hubner) (Lepidoptera: Noctuidae), *Appl. Environ. Microbiol,*. Vol. 61, pp. 2086–2092.

S. M. Mohamed, Unpublished data, 1999.

J. Muller-Cohn et al., *Spodoptera littoralis* (Lepidoptera: Noctuidae) resistance to Cry1C and cross-resistance to other *Bacillus thuringiensis* crystal toxins, *J. Econ. Entomol.,* Vol. 89, pp. 791–797, 1996.

Y. Nagamatsu et al., Cloning, sequencing, and expression of the *Bombyx mori* receptor for *Bacillus thuringiensis* insecticidal Cry1A(a) toxin, *Biosci. Biotechnol. Biochem.,* Vol. 62, pp. 727–734.

Y. Nagamatsu et al., Identification of *Bombyx mori* midgut receptor for *Bacillus thuringiensis* insecticidal Cry1A(a) toxin, *Biosci. Biotechnol. Biochem,*. Vol. 62, pp. 718–726, 1998.

P. H. O'Farrell, High resolution two-dimensional electrophoresis of proteins, *J. Biol. Chem,*. Vol. 250, pp. 4007–4021, 1975.

B. Oppert et al., Luminal proteinases from *Plodia interpunctella* and the hydrolysis of *Bacillus thuringiensis* Cry1A (c) protoxin, *Insect Biochem. Mol. Biol,*. Vol. 26, pp. 571–583, 1996.

J. J. Peluso et al., N-cadherin-mediated cell contact inhibits granulosa cell apoptosis in a progesterone-independent manner, *Endocrinology*, Vol. 137, pp. 1196–1203, 1996.

F. J. Perlak et al., Insect resistant cotton plants, *Biotechnology* (NY), Vol. 8, pp. 939–943, 1990.

C. T. Powell et al., Persistent membrane translocation of protein kinase C alpha during 12-0-tetradecanoylphorbol-13-acetate-induced apoptosis of LNCaP human prostate cancer cells, *Cell Growth Differ,*. Vol. 7, pp. 419–428, 1996.

D. L. Rimm et al., Molecular cloning of human E-cadherin suggests a novel subdivision of the cadherin superfamily, *Biochem. Biophys. Res. Commun,*. Vol. 200, pp. 1754–1761, 1994.

J. Sambrook et al., Molecular Cloning: a laboratory manual, 2$^{nd}$ ed., Cold Spring Harbor Laboratory, Cold Spring Harbor, N.Y., 1989.

E. Schnepf et al., *Bacillus thuringiensis* and its pesticidal crystal proteins, *Microbiol. Mol. Biol. Rev,*. Vol. 62, No. 3, pp. 775–806, 1998.

J. L. Schwartz et al., Single-site mutations in the conserved alternating-arginine region affect ionic channels formed by Cry1Aa, a *Bacillus thuringiensis* toxin, *Appl. Environ. Microbiol,*. Vol. 63, pp. 3978–3984, 1997.

T. Shimizu et al., Lamin B phosphorylation by protein kinase calpha and proteolysis during apoptosis in human leukemia HL60 cells, *J. Biol. Chem,*. Vol. 273, No. 15, pp. 8669–8674, 1998.

S. Strehl et al., Characterization of two novel protocadherins (PCDH8 and PCDH9) localized on human chromosome 13 and mouse chromosome 14, *Genomics*, Vol. 53, No. 1, pp. 81–89, 1998.

S. T. Suzuki, Protocadherins and diversity of the cadherin superfamily, *J. Cell, Sci,.* Vol. 109 (Pt. 11), pp. 2609–2611, 1996.

B. E. Tabashnik et al., Reversal of resistance to *Bacillus thuringiensis* in *Plutella xylstella*, *PNAS* USA, Vol. 91, No. 10, pp. 4120–4124, 1994.

M. Takeichi et al., Cadherin-mediated cell-cell adhesion and neurogenesis, *Neurosci. Res. Suppl,*. Vol. 13, pp. S92–S96, 1990.

R. K. Vadlamudi et al., A specific binding protein from *Manduca sexta* for the insecticidal toxin of *Bacillus thuringiensis* subsp. *berliner,*. J. Biol. Chem., Vol. 268, No. 17, pp. 12334–12340, 1993.

R. K. Vadlamudi et al., Cloning and expression of a receptor for an insecticidal toxin of *Bacillus thuringiensis, J. Biol. Chem,*. Vol. 270, No. 10, pp. 5490–5494, 1995.

A. P. Valaitis et al., Interaction analyses of *Bacillus thuringiensis* Cry1A toxins with two aminopeptidases from gypsy moth midgut brush border membranes, *Insect Biochem. Mol. Biol,*. Vol. 27, pp. 529–539, 1997.

A. P. Valaitis et al., Brush border membrane aminopeptidase-N in the midgut of the gypsy moth serves as the receptor for the Cry1A(c) delta-endotoxin of *Bacillus thuringiensis, Insect Biochem. Mol. Biol,*. Vol. 25, No. 10, pp. 1143–1151, 1995.

T. F. Watson et al., Presented at the Beltwide Cotton Conf., Memphis.

M. E. Whalon et al., Selection of a Colorado potato beetle (Coleoptera: Chysomelidae) strain resistant to *Bacillus thuringiensis, J. Econ. Entomol,*. Vol. 86, pp. 226–233, 1993.

M. R. Williams, Presented at the Beltwide Cotton Conf., 1999.

G. K. Winkel et al., Activation of protein kinase C triggers premature compaction in the four-cell stage mouse embryo, *Dev. Biol,*. Vol. 138, pp. 1–15, 1990.

M. G. Wolfersberger, The toxicity of two *Bacillus thuringiensis* δ-endotoxins to gypsy moth larvae is inversely related to the affinity of binding sites on midgut brush border membrane for the toxins, *Experientia*, Vol. 46, pp. 475–477, 1990.

M. Wolfersberger et al., Preparation and partial characterization of amino acid transporting brush border membrane vesicles from the larval midgut of the cabbage butterfly (*Pieris brassicae*), *Comp. Biochem. Physiol,*. Vol. 86A, pp. 301–308, 1987.

K. Yaoi et al., Aminopeptidase N from *Bombyx mori* as a candidate for the receptor of *Bacillus thuringiensis* Cry1Aa toxin, *Eur. J. Biochem,*. Vol. 246, pp. 652–657, 1997.

While this invention has been described with reference to illustrative embodiments, this description is not intended to

What is claimed is:

1. An isolated protein which binds cry1 A(c), wherein said protein comprises
   a) the amino acid sequence at positions 1269–1367 of SEQ. ID. No.: 2; or
   b) the amino acid sequence at positions 24–1729 of SEQ. ID. No.: 2.; or
   c) an amino acid sequence at least 95% homologous to positions 1–1729 of SEQ. ID. No.: 2.

2. The isolated protein of claim 1, wherein the protein comprises the amino acid sequence at positions 1269–1367 of SEQ. ID. No.: 2.

3. The isolated protein of claim 1, wherein the protein comprises the amino acid sequence at positions 24–1729 of SEQ. ID. No.: 2.

4. The isolated protein of claim 1, wherein the protein comprises an amino acid sequence at least 95% homologous to positions 1–1729 of SEQ. ID. No.: 2.

5. The isolated protein of claim 4, which comprises the amino acid sequence of positions 1–1729 of SEQ. ID. No.: 2.

6. A method to identify a candidate pesticide against *P. gossypiella*, which method comprises contacting a test compound with the protein of claim 1 and assessing the ability of said test compound to bind to said protein
   wherein a test protein that binds to said protein is identified as a candidate pesticide against *P. gossypiella*.

* * * * *